United States Patent [19]
Cook et al.

[11] 3,975,376
[45] Aug. 17, 1976

[54] PENCILLINS HAVING A 6β-(α-ETHERIFIED OXIMINO) ACYLAMIDO GROUP

[75] Inventors: Martin Christopher Cook; Gordon Ian Gregory, both of Chalfont St. Peter; Janice Bradshaw, Harrow, all of England

[73] Assignee: Glaxo Laboratories Limited, Greenford, England

[22] Filed: Oct. 31, 1975

[21] Appl. No.: 627,905

Related U.S. Application Data

[60] Division of Ser. No. 304,501, Nov. 7, 1972, Pat. No. 3,932,385, which is a continuation-in-part of Ser. No. 252,846, May 12, 1972, abandoned.

[30] Foreign Application Priority Data

May 14, 1971 United Kingdom............... 15082/71
Oct. 25, 1972 United Kingdom............... 49256/72

[52] U.S. Cl................................ 260/239.1; 424/271
[51] Int. Cl.²........................................ C07D 499/70
[58] Field of Search................................ 260/239.1

[56] References Cited
OTHER PUBLICATIONS
Moses et al., Arkiv För Kemi, 22 (33), 451–467, (1964).
Ekström et al., Acta Chemica Scandinavica 19, 281–299, (1965).

Primary Examiner—Gerald A. Schwartz
Attorney, Agent, or Firm—Bacon & Thomas

[57] ABSTRACT

The invention provides novel antibiotic compounds which are 6β-acylamidopenam-3-carboxylic acids, and nontoxic derivatives thereof, characterized in that the acylamido group has the structure

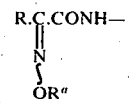

where R is a hydrogen atom or an organic group and $R''$ is an etherifying monovalent organic group linked to the oxygen atom through a carbon atom. The compounds may be either syn or anti isomers or may exist as mixtures e.g. containing at least 75% of one isomer. These antibiotic compounds possess high antibacterial activity against a range of gram positive organisms including penicillinase - producing staphylococci coupled with high activity against strains of the gram-negative organism *Haemophilus influenzae*. The invention is also concerned with the administration of the compounds.

11 Claims, No Drawings

PENCILLINS HAVING A 6β-(α-ETHERIFIED OXIMINO) ACYLAMIDO GROUP

Cross Reference to Related Application

This application is a division of copending application Ser. No. 304,501, now U.S. Pat. No. 3,932,385, which is in turn a continuation-in-part of application Ser. No. 252,846, filed May 12, 1972 and now abandoned.

This invention is concerned with improvements in or relating to antibiotics of the penicillin series.

The penicillin compounds referred to in this specification are generally named with reference to penam (*J. Amer. Chem. Soc.* 1953, 75, 3293).

As is well known, antibiotics of the penicillin series are 6β-acylamidopenam-3α-carboxylic acids and their various non-toxic derivatives e.g. salts, esters, amides, hydrates or the corresponding sulphoxides. Substitution may, for example, be present on at least one of the gem-dimethyl groups.

The new compounds of the present invention are characterized in that said acylamido group of the penicillin antibiotic is an (α-etherified oximino) acylamido group. The compounds may be either syn or anti isomers or mixtures thereof, especially mixtures wherein one isomeric form predominates.

According to one embodiment of the invention, therefore, we provide 6β-acylamidopenam-3α-carboxylic acids (and non-toxic derivatives thereof) characterized in that said acylamido group has the structure:

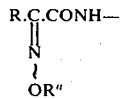

where R is a hydrogen atom or an organic group and $R^a$ is an etherifying monovalent organic group linked to the oxygen atom through a carbon atom. The compounds of the invention may be either syn or anti isomers or mixtures thereof, especially such mixtures which contain at least 75% of one such isomer. Preferably, the mixtures of isomers contain at least 90% of one of the isomers and not more than 10% of the other.

The compounds of the invention are defined as having the syn (cis) or anti (trans) isomeric form as regards the configuration of the group $OR^a$ with respect to the carboxamido group. In this specification, the syn configuration is structurally denoted thus:

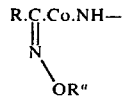

and the anti configuration thus:

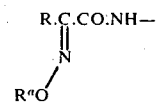

These configurations are assigned on the basis of the work of Ahmad and Spencer (*Can. J. Chem.*, 1961, 39, 1340).

The 6β-acylamidopenam-3α-carboxylic acids of the invention may be defined by the formula:

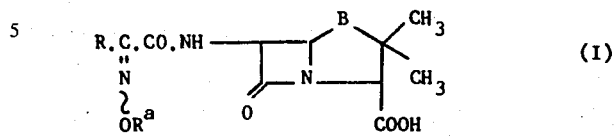

wherein R and $R^a$ have the above-defined meanings and B is $> S$ or $> S \rightarrow O$, preferably $> S$. The invention also includes compounds not specifically embraced by formula (I) e.g. 2β-acetoxymethyl penicillins.

The term "non-toxic" as applied to the derivatives of the compounds of the invention means those derivatives which are physiologically acceptable in the dosage at which they are administered.

Salts which may be formed, where applicable, from the compounds according to the invention include (a) inorganic base salts such as alkali metal, e.g. sodium and potassium, alkaline earth metal e.g. calcium, and organic base, e.g. procaine, phenylethylbenzylamine, dibenzylethylene diamine ethanolamine, diethanolamine, and N-methylglucosamine, salts and (b) acid addition salts e.g., with hydrochloric, hydrobromic, sulphuric, nitric, phosphoric, toluene-p-sulphonic and methane sulphonic acids. The salts may also be in the form of resinates, formed e.g., with a polystyrene resin containing amino, quaternary amino, or sulphonic acid groups, or a resin containing carboxyl groups, e.g. a polyacrylic acid resin. The resin may if desired be cross-linked, e.g. it may be a copolymer of styrene and divinyl-benzene containing the appropriate groups. Additionally, the derivatives may be in the form of a chelate with a heavy metal such as iron or copper.

The compounds of the invention, including the non-toxic derivatives thereof, possessing the syn configuration, are characterized by their high antibacterial activity against a range of gram-positive organisms including penicillinase-producing staphylococci coupled with high activity against strains of the gram-negative organism *Haemophilus influenzae*.

The compounds of the invention possessing the syn configuration generally possess high stability to β-lactamases of the type produced by the gram-negative organism *Enterobacter cloacae* P99 and in various instances also as will appear hereinafter, high stability to β-lactamases produced by staphylococcal organisms. Further, certain of the syn compounds, as will also appear hereinafter, possess the property of oral absorption on administration as evidenced by animal tests.

The properties described above render the syn compounds of the invention particularly useful in the treatment of a variety of diseases caused by pathogenic bacteria in human beings and animals. For example, by suitable selection of properties, various of the syn compounds of the invention are useful in the treatment of upper respiratory tract infections. Again, various of the syn compounds of the invention are useful in the treatment of bovine udder infections by means of intramammary preparations.

The compounds of the invention, including the non-toxic derivatives thereof, possessing the anti configuration have been found by us to possess anti-bacterial activity against various gram-positive organisms coupled with activity against strains of *Haemophilus influenzae*.

The group $R^a$ in the above formulae may be a group having a carbon atom with one free valency so that it forms the desired ether group with the adjacent oxygen atom. The group $R^a$ desirably contains not more than 16 carbon atoms.

$R^a$ may thus be, for example, an alkyl group containing 1–16 carbon atoms, particularly a lower alkyl group containing 1–8 carbon atoms, e.g. a methyl, ethyl, n-propyl, iso-propyl, n-butyl, iso-butyl, sec-butyl, t-butyl, octyl or dodecyl group; an alkenyl group containing 2–16 carbon atoms, preferably 2–8 carbon atoms, e.g. a vinyl, allyl, isopropenyl, or dimethylallyl group; an alkynyl group containing 2–16 carbon atoms, preferably 2–8 carbon atoms, e.g. a propynyl group such as propargyl; a cycloalkyl group containing 3–7 carbon atoms, e.g. a cyclopropyl, cyclopentyl or cyclohexyl group; a cycloalkenyl group containing 4–7 carbon atoms, e.g. a cyclopentenyl, cyclohexenyl, cyclopentadienyl group or cyclohexadienyl; a carbocyclic aryl group, e.g. a phenyl or naphthyl group; a heterocyclic group containing at least one hetero atom selected from oxygen, nitrogen and sulphur, e.g. a pyridyl, pyrimidyl, furyl, thienyl, thiazolyl, thiadiazolyl, diazolyl, triazolyl, tetrazolyl, thiatriazolyl, oxazolyl, oxadiazolyl, benzimidazolyl, benzoxazolyl or purinyl group; or a carbocyclic or heterocyclic aryl lower alkyl group in which the lower alkyl portion contains 1–4 carbon atoms, e.g. a benzyl, phenethyl, diphenylmethyl, triphenylmethyl, thienylmethyl such as thien-2-ylmethyl, furylmethyl such as furfuryl, pyridylmethyl, or pyrrolylmethyl group.

In general $R^a$ may be unsubstituted or may carry one or more substituents such as, for example, hydroxy; alkoxy, e.g. methoxy, ethoxy, n-propoxy or iso-propoxy, as in, for example, methoxymethyl or 1-ethoxyethyl; aryloxy, e.g. phenoxy; aralkoxy, e.g. benzyloxy; mercapto; alkylthio, e.g. methylthio or ethylthio; arylthio; aralkylthio; amino as in, for example, 2-aminoethyl; substituted amino, e.g. methylamino, ethylamino or dimethylamino; halo, e.g. chloro or bromo, as in, for example, 2-bromoethyl; nitro; azido; carboxy; esterified carboxy, e.g. lower alkoxy carbonyl such as methoxycarbonyl or ethoxycarbonyl, or benzyloxycarbonyl; formyl; acyl, e.g. acetyl, propionyl or benzoyl; acyloxy e.g. acetoxy, propionyloxy or pivaloyloxy; cyano; phthalimido; acylamido, e.g. acetamido or benzamido; alkoxycarbonylamino, e.g. methoxycarbonylamino or ethoxycarbonylamino; or aralkoxycarbonylamino, e.g. benzyloxycarbonylamino.

The group R in the above general formulae may be chosen from the following list which is not intended to be exhaustive:

i. Hydrogen, ii. $R^u$, where $R^u$ is aryl (carbocyclic or heterocyclic), cycloalkyl, substituted aryl, substituted cycloalkyl, cycloalkadienyl, or a non-aromatic or mesionic group. Examples of this group include phenyl; naphthyl e.g. naphth-1-yl; phenyl or naphthyl substituted by halo e.g. chloro or bromo as in o-chlorophenyl, hydroxy, lower alkyl e.g. methyl, nitro, amino, lower alkylamino e.g. methylamino, diloweralkylamino e.g. dimethylamino, lower alkanoyl e.g. acetyl, lower alkanoylamido lower alkoxy e.g. methoxy or ethoxy, or lower alkylthio e.g. methylthio; a 5- or 6- membered heterocyclic group containing at least one hetero atom selected from S, N and O e.g. thien-2-yl, thien-3-yl, furyl such as fur-2-yl, pyridyl such as pyrid-3-yl, pyrrolyl, N-substituted pyrrolyl e.g. N-methylpyrrolyl, or N-benzyloxymethylpyrrolyl, isothiazolyl, thiadiazolyl, oxadiazolyl, 3- or 4-isoxazolyl; substituted 3- or 4-isoxazolyl e.g. 3-aryl-5-methylisoxazol-4-yl, the aryl group being e.g. phenyl or halophenyl; fused heterocyclic groups containing at least one hetero atom selected from S, N and O, e.g. benzothienyl such as benzothien-3-yl, benzofuryl, indolyl; cyclohexyl; cyclopentyl; sydnene; and cyclohexadienyl.

iii. $R^u(CH_2)_mQ_n(CH_2)_p$ where $R^u$ has the above defined meaning and $m$ is 0 or an integer from 1 to 4, $n$ is 0 or 1, $p$ is an integer from 1 to 4 and Q is S, O or NR wherein R is hydrogen or an organic group e.g. alkyl such as methyl or aryl such as phenyl. Examples of this group include methyl, ethyl or butyl substituted by the various specific $R^u$ groups listed under (ii) e.g. benzyl and the appropriate substituted benzyl groups.

iv. $C_nH_{2n+}$ wherein $n$ is an integer from 1 to 7. The group may be straight or branched and, if desired, may be interrupted by an oxygen or sulphur atom or the group NR wherein R is hydrogen or an organic group e.g. alkyl such as methyl or aryl such as phenyl; or be substituted by a cyano, carboxy, alkoxycarbonyl, hydroxy or carboxycarbonyl (HOOC.CO.) group or by a halogen atom. Examples of such groups include hexyl, heptyl, butylthiomethyl, cyanomethyl or trihalomethyl.

v. $C_nH_{2n-1}$ where $n$ is an integer from 2 to 7. The group may be straight or branched and, if desired, may be interrupted by an oxygen or sulphur atom or the group NR wherein R is hydrogen or an organic group e.g. alkyl such as methyl or aryl such as phenyl. An example of such a group is vinyl or propenyl.

vi. $C_nH_{2n-3}$ where $n$ is an integer from 2 to 7. An example of such a group is ethynyl.

vii. Miscellaneous carbon-linked organic groups including cyano, amido and lower alkoxycarbonyl.

Important antibiotic compounds according to the invention by virtue of their being active against a wide variety of gram-positive organisms (penicillin-resistant and penicillin sensitive strains of *Staph. aureus*) and possessing activity against *Haemophilus influenzae* are those having the general formula

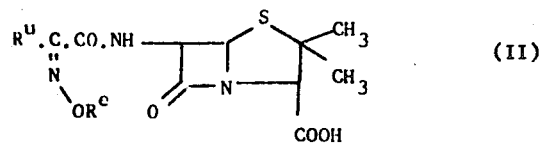

(II)

[wherein $R^u$ is phenyl; naphthyl; thienyl; furyl; benzothienyl, benzofuryl or N-methylpyrrolyl or any or these groups substituted by halo (chloro, bromo, iodo or fluoro), hydroxy, lower alkyl, nitro, amino, loweralkylamino, diloweralkylamino, lower alkanoyl, lower alkanoylamido, lower alkoxy, lower alkylthio or carbamoyl and $R^e$ is $C_1$-$C_8$ alkyl, cyclopentyl, phenyl, benzyl, phenethyl, thienylmethyl, furylmethyl or lower (alkoxy-alkyl)] and non-toxic derivatives thereof.

Particularly important compounds of general formula (II) by virtue of their uniformly high activity against gram-positive organisms coupled with activity against *Haemophilus influenzae* are those having the formula

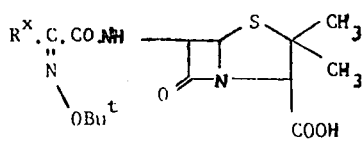 (III)

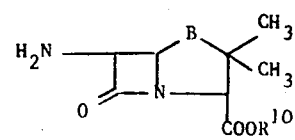 (V)

(wherein $R^x$ is phenyl; naphthyl; thienyl; furyl; benzothienyl or benzofuryl and $Bu^t$ is tert.-butyl) and non-toxic derivatives thereof, especially as their sodium or potassium salts. These compounds also exhibit high stability to β-lactamases of the type produced by *E. clocae* P99, *E. coli* TEM and by staphylococcal organisms.

An important group of compounds falling within general formula II are those having the general formula

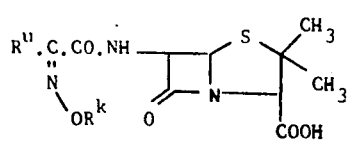 (IV)

(wherein $R^u$ is as defined above for formula (II) and $R^k$ is methyl or ethyl) and non-toxic derivatives thereof. In addition to possessing the stated properties of the compounds of formula (II), the compounds of formula (IV) also possess the important property of significant absorption on oral administration as evidenced by animal tests.

Important compounds falling within general formula (IV) include the following compounds in their syn isomeric form:

6β-(2-methoxyimino-2-phenylacetamido)-2,2-dimethylpenam-3α-carboxylic acid;
6β-[2-ethoxyimino-2-phenylacetamido]-2,2-dimethylpenam-3α-carboxylic acid;
6β-[2-methoxyimino-2-(thien-2-yl)acetamido]-2,2-dimethylpenam-3α-carboxylic acid;
6β-[2-ethoxyimino-2-(thien-2-yl)acetamido]-2,2-dimethylpenam-3α-carboxylic acid;
6β-[2-methoxyimino-2-(naphth-1-yl)acetamido]-2,2-dimethylpenam-3α-carboxylic acid;
6β-[2-methoxyimino-2-(2-chlorophenyl)acetamido]-2,2-dimethylpenam-3α-carboxylic acid, 6β-[2-methoxyimino-2-(1-methylpyrrol-2-yl)acetamido]-2,2-dimethylpenam-3α-carboxylic acid, especially as their sodium, potassium or diethanolamine salts.

Preparation

The compounds according to the invention may be prepared by any convenient method. According to one embodiment of the invention we provide a process for the preparation of a compound of the formula

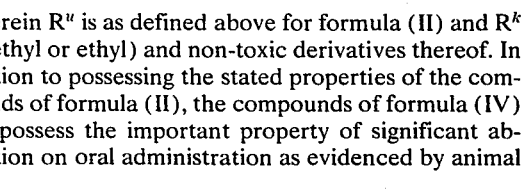 (I)

(wherein R is a hydrogen atom or an organic group, $R^a$ is an etherifying monovalent organic group linked to the oxygen atom through a carbon atom and B is > S or > S → O) and derivatives thereof, which comprises either (A) condensing a compound of the formula (wherein B has the above defined meaning and $R^{10}$ is hydrogen or a carboxyl blocking group) with an acylating agent, advantageously either as the syn isomer or as the anti isomer, corresponding to the acid

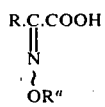 R.C.COOH (VI)
N
OR"

(wherein R and $R^a$ have the above defined meanings) or with an acylating agent corresponding to an acid which is a precursor for the acid VI; or (B) reacting a compound of the formula

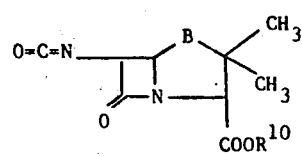 (VII)

(wherein B and $R^{10}$ have the above defined meanings except that $R^{10}$ is not hydrogen) with an acid, or precursor of formula VI; whereafter, if necessary and desired in each instance, any of the following reactions (C) are carried out (i) conversion of a precursor for the desired

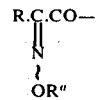 R.C.CO—
N
OR"

group into that said group (ii) removal of any carboxyl blocking groups and (iii) reduction of a compound in which B is > S → O to form the desired B= > S compound and (D) recovering the desired compound of formula (I), after separation of isomers if desired.

Salts of the compounds according to the invention may be formed in any convenient way. For example base salts may be formed by reaction of the penicillin acid with sodium or potassium 2-ethylhexanoate.

In practice it is convenient to condense an acylating agent corresponding to the acid

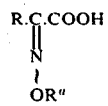 R.C.COOH (VI)
N
OR"

where R and $R^a$ have the above defined meanings, with an amino compound

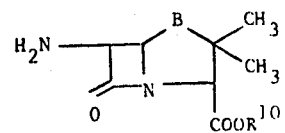 (V)

[where B has the above defined meaning and $R^{10}$ is hydrogen or a carboxyl blocking group e.g. the residue of an ester-forming alcohol (aliphatic or araliphatic), phenol, silanol, stannanol or acid] the condensation, if desired, being effected in the presence of a condensation agent, and being followed, if necessary, by removal of the group $R^{10}$. There may also be used, if desired, a derivative of the compound of formula (V) such as a salt e.g. a tosylate.

The compounds of formula I may thus be prepared by employing as the acylating agent an acid halide, particularly an acid chloride or bromide. The acylation may be effected at temperatures of from $-50°$ to $+50°C$, preferably $-20°$ to $+30°C$. The acylating agent may be prepared by reacting the acid (VI) or a salt thereof with a halogenating agent e.g. phosphorus pentachloride, thionyl chloride or oxalyl chloride. Use of oxalyl chloride with the sodium or potassium salt of the acid (VI) is preferred since under these conditions isomerisation is minimal. The acylation may be effected in aqueous or non-aqueous media and suitable media include an aqueous ketone such as aqueous acetone, an ester e.g. ethyl acetate, or an amide e.g. dimethylacetamide, or a nitrile e.g. acetonitrile, or mixtures thereof.

Acylation with an acid halide may be effected in the presence of an acid binding agent e.g. a tertiary amine (e.g. triethylamine or dimethylaniline), an inorganic base (e.g. calcium carbonate or sodium bicarbonate) or an oxirane, which binds hydrogen halide liberated in the acylation reaction. The oxirane is perferably a lower-1,2-alkylene oxide e.g. ethylene oxide or propylene oxide.

When using the free acid form of a compound of formula (VI), suitable condensing agents for use in the preparation of the compounds according to the invention include carbodiimides, for example N,N'-diethyl-, dipropyl- or diisopropylcarbodiimide, N,N'-dicyclohexylcarbodiimide, or N-ethyl-N'-γ-dimethylaminopropylcarbodiimide; a suitable carbonyl compound, for example carbonyldiimidazole; or an isoxazolinium salt, for example, N-ethyl-5-phenylisoxazolinium-3'-sulphonate and N-t-butyl-5-methylisoxazolinium perchlorate. The condensation reaction is desirably effected in an anhydrous reaction medium, e.g. methylene chloride, dimethylformamide or acetonitrile, since one may then regulate more precisely reaction parameters such as temperature.

Alternatively, acylation may be effected with other amide-forming derivatives of the free acid such as, for example, a symmetrical anhydride or mixed anhydride, e.g. with pivalic acid or formed with a haloformate, e.g. a lower alkylhaloformate. The mixed or symmetrical anhydrides may be generated in situ. For example, a mixed anhydride may be generated using N-ethoxycarbonyl-2-ethoxy-1,2-dihydroquinoline. Mixed anhydrides may also be formed with phosphorus acids (for example phosphoric or phosphorous acids), sulphuric acid or aliphatic or aromatic sulphonic acids (for example p-toluenesulphonic acid). Another convenient acylating agent is an activated ester e.g. a compound of the formula

   (VIII)

where L, is for example, an azide, oxysuccinimide, oxybenztriazole, pentachlorophenoxy or p-nitrophenoxy group.

Alternatively the compound of formula (I) may be prepared from a compound of formula

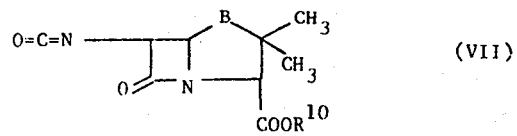   (VII)

(where B and $R^{10}$ have the above defined meanings except that $R^{10}$ is not hydrogen) by reaction with an acid, or precursor, of formula (VI) and subsequently removing the group $R^{10}$ (see for example Dutch patent application No. 6808622).

If desired, one can first prepare a compound of formula

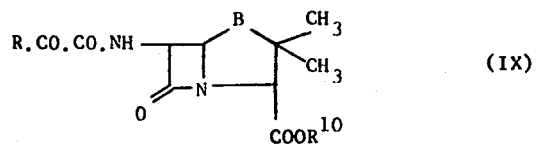   (IX)

(where R, $R^{10}$ and B have the above defined meanings) and then effect reaction of the compound of formula (IX) with $R^aO.NH_2$ ($R^a$ having the above defined meaning), followed, if necessary by removal of the group $R^{10}$. The reaction product may be separated into syn and anti isomers before or after removal of $R^{10}$.

A useful precursor of the desired

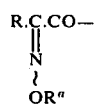

group is the corresponding 2-hydroxyiminoacyl group

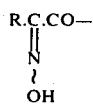

since this may readily be converted to the desired group by etherification. Thus compounds of formula (I) may be prepared by reacting a compound of formula

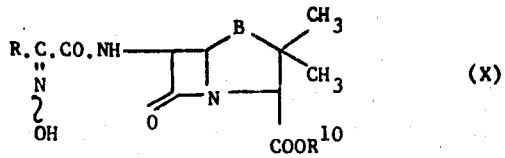   (X)

wherein R, $R^{10}$ and B are as hereinbefore defined, with an etherifying agent serving to introduce the group $R^a$ and subsequently if necessary and desired carrying out either of reactions C(ii) or C(iii) described above and recovering the desired compound of formula (I) after separation of isomers if necessary.

The etherifying agent may be, for example, an organic halide or sulphate, or a sulphonate such as tosylate. Other etherifying agents include diazoalkanes, e.g. diazomethane or diazoethane, alkyl fluorosulphonates, e.g. methyl fluorosulphonate, alkyloxonium tetrafluoroborates, e.g. a trialkyloxonium tetrafluoroborate such as triethyloxonium tetrafluoroborate and diphenyliodonium bromide. Etherification using a diazo compound, fluorosulphonate or tetrafluoroborate may require assistance, e.g. with a Lewis acid such as $BF_3$.

One may prepare compounds of formula (I) wherein R is an activating group such as cyano or 2- or 4-pyridyl by a technique involving nitrosation and etherification of the resulting oxime. Thus a compound possessing the acylamido group

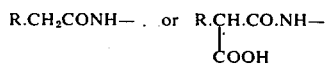

where R is an activating group may be nitrosated using, for example, nitrous acid (which may be prepared in situ by reaction of an alkali metal nitrite with a weak acid e.g. acetic acid), nitrosyl chloride, or an organic nitrosating agent e.g. an alkyl, cycloalkyl, or aralkyl nitrite. In the case of nitrosation of a compound containing the group

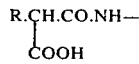

decarboxylation will occur. Separation of syn and anti-isomers may be necessary after the nitrosation or etherification reaction.

Compounds of the formula (V) may be employed as esters; those of formula (VII) are esters. One may also use the free amino acid or an acid addition salt of the free amino acid or ester thereof. Salts which may be used include acid addition salts e.g. with hydrochloric, hydrobromic, sulphuric, nitric, phosphoric, toluene-p-sulphonic and methane sulphonic acids.

The ester may be formed with an alcohol, phenol, silanol or stannanol having up to 20 carbon atoms which may readily be split off at a later stage of the overall reaction.

Any esterifying group substituting the 3-carboxyl group of a compound of formula (V), (VII) or (IX) is preferably formed with an alcohol (aliphatic or aralipathic), phenol, silanol, stannanol or acid which may readily be split off at a later stage of the reaction.

Suitable esters thus include compounds containing as ester group a group selected from the following list which is not intended to be an exhaustive list of possible ester groups.

i. — $COOCR^fR^gR^h$ wherein at least one of $R^f$, $R^g$ and $R^h$ is an electron-donor e.g. p-methoxyphenyl, 2,4,6-trimethylphenyl, 9-anthryl, methoxy, acetoxy, or fur-2-yl. The remaining $R^f$, $R^g$ and $R^h$ groups may be hydrogen or organic substituting groups. Suitable ester groups of this type include p-methoxybenzyloxycarbonyl and 2,4,6-trimethylbenzyloxy carbonyl.

ii. — $COOCR^fR^gR^h$ wherein at least one of $R^f$, $R^g$ and $R^h$ is an electron-attracting group e.g. benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. The remaining $R^f$, $R^g$, and $R^h$ groups may be hydrogen or organic substituting groups. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

iii. — $COOCR^fR^gR^h$ wherein at least two of $R^f$, $R^g$ and $R^h$ are hydrocarbon such as alkyl e.g. methyl or ethyl, or aryl e.g. phenyl and the remaining $R^f$, $R^g$ and $R^h$ group, if there is one, is hydrogen. Suitable esters of this type include t-butyloxycarbonyl, t-amyloxycarbonyl, diphenylmethoxycarbonyl and triphenylmethoxycarbonyl.

iv. — $COOR^i$ wherein $R^j$ is adamantyl, 2-benzyloxyphenyl, 4-methylthiophenyl, tetrahydrofur-2-yl or tetrahydropyran-2-yl.

v. Silyloxycarbonyl groups obtained by reaction of a carboxyl group with a derivative of a silanol. The derivative of a silanol is conveniently a halosilane or a silazane of the formula
$R^{11}_3SiD$; $R^{11}_2SiD_2$; $R^4_3Si.NR^4_2$; $R^{11}_3Si.NH.SiR^{11}_3$; $R^{11}_3Si.NH.COR^{11}$; $R^{11}_3Si.NH.CO.NH.SiR^{11}_3$; $R^{11}NH.CO.NR^{11}.SiR^{11}_3$; or $R^{11}C(OSiR^{11}_3)$: $NSiR^{11}_3$ where D is a halogen and the various groups $R^{11}$, which can be the same or different, represent hydrogen atoms or alkyl, e.g. methyl, ethyl, n-propyl, iso-propyl; aryl, e.g. phenyl; or aralkyl e.g. benzyl groups. Preferred derivatives of silanols are silyl chlorides such as for example trimethylchlorosilane and dimethyldichlorosilane.

The carboxyl group may be regenerated from an ester by any of the usual methods, for example, acid- and base-catalysed hydrolysis is generally applicable, as well as enzymically-catalysed hydrolyses; however, aqueous mixtures may be poor solvents for these compounds and they may cause isomerizations, rearrangements, side-reactions, and general destruction, so that special methods may be desirable.

Five suitable methods of deesterification are:

1. Reactions with Lewis acids.

Suitable Lewis acids for reaction with the esters include trifluoroacetic acid, formic acid, hydrochloric acid in acetic acid, zinc bromide in benzene and aqueous solutions or suspensions or mercuric compounds. The reaction with the Lewis acid may be facilitated by addition of a nucleophile such as anisole.

2. Reduction.

Suitable systems for effecting reduction are zinc/acetic acid, zinc/formic acid, zinc/lower alcohol, zinc/pyridine, palladised-charcoal and hydrogen, and sodium and liquid ammonia.

3. Attack by nucleophiles.

Suitable nucleophiles are those containing a nucleophilic oxygen or sulphur atom for example alcohols, mercaptans and water.

4. Oxidative methods, for example, those which involve the use of hydrogen peroxide and acetic acid.

5. Irradiation.

Where at the end of a given preparative sequence compounds are obtained wherein B is $> S \rightarrow O$ and a compound is desired in which B is $> S$ conversion to a sulphide may for example, be effected by reduction of the corresponding acyloxysulphonium or alkyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid, tetrahydrofuran, dioxan, dimethylformamide or dimethylacetamide. The reaction may be effected at a temperature of −20° to +50°C.

Alternatively, reduction of the 1-sulphinyl group may be effected by phosphorus trichloride or tribromide in solvents such as methylene chloride, dimethylformamide or tetrahydrofuran, preferably at a temperature of −20°C The acid (VI) to which the acylating agent corresponds may be obtained by reacting a glyoxylic acid of formula

R.CO.COOH (where R has the above defined meaning) or an ester thereof with R″O.NH₂ (R″ having the above defined meaning).

The resulting acid or ester may then be separated into its syn and anti isomers e.g. by crystallisation, chromatography or distillation, followed when necessary by hydrolysis of the ester.

Separation of the syn and anti components of an ester derivative of an α(-etherified oximino)carboxylic acid existing as a mixture of the syn and anti isomers may be effected by selective hydrolysis of the ester under basic conditions, since the less sterically hindered anti isomer tends to saponify more rapidly and may thus be removed as the free acid, leaving purified syn ester. The separated syn ester may then be converted to a corresponding acylating agent as desired. This process as described in greater detail in copending application Ser. No. 304,491 of Janice Bradshaw and Godfrey Basil Webb filed on even date herewith now U.S. Pat. No. 3,932,385.

The acid (VI) may also be prepared by carrying out an O-alkylation or O-arylation type of reaction on a compound of the formula

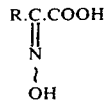

i.e. a 2-hydroxyimino acid or on an ester of such a 2-hydroxyimino acid. The desired reaction may be achieved with an organic halide, sulphate or sulphonate, e.g. a compound of formula R″J where R″ has the above-defined meaning and J is halogen, sulphate or a sulphonate such as tosylate. Alternatively the 2-hydroxyimino acid or an ester thereof may be reacted with a diazoalkane, e.g. diazomethane, an alkyl fluorosulphonate, e.g. methyl fluorosulphonate, or an alkyloxonium tetra-fluoroborate, e.g. a trialkyloxonium tetrafluoroborate such as triethyloxonium tetrafluoroborate to give the required alkoxyimino acid (VI) or with diphenyliodonium bromide to give the required phenoxyimino acid (VI) or an ester thereof. Such reactions with a diazo compound, fluorosulphonate or tetrafluoroborate may require assistance, e.g. with a Lewis acid such as BF₃.

When converting the acid (VI) to a corresponding acylating agent it will be appreciated that any amino groups present in R or R″ should desirably be protected to avoid undesirable side reactions; similar protection of amino groups is also desirable when reacting the consequent acylating agent with a compound of formula (V) or (VII).

Syn and anti isomers may be distinguished by appropriate techniques, e.g. by their ultraviolet spectra, by thin layer or paper chromatography or by their nuclear magnetic resonance spectra. For example, for DMSO-d₆ solution compounds of Formula I exhibit the doublet for the amide NH at a lower field for the syn isomers than for the anti-isomers. These factors may be employed in monitoring reactions.

The antibacterial compounds according to the invention may be formulated for administration in any convenient way, by analogy with other antibiotics and the invention therefore includes within its scope a pharmaceutical composition comprising an antibacterial compound of formula I or a non-toxic derivative e.g. salt thereof (as herein defined) adapted for use in human or veterinary medicine. Such compositions may be presented for use in conventional manner with the aid of any necessary pharmaceutical carriers or excipient.

The antibacterial compounds according to the invention may be formulated for injection and may be presented in unit dose form in ampoules, or in multi-dose containers with an added preservative. The compositions may take such forms as suspensions, solutions, emulsions in oily or aqueous vehicles, and may contain formulatory agents such as suspending, stabilising and-/or dispersing agents. Alternatively the active ingredient may be in powder form for reconstitution with a suitable vehicle, e.g. sterile, pyrogen-free water before use.

The compositions may be presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinyl-pyrollidone; fillers, for example lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparation may be in the form of aqueous or oily suspensions, solutions, emulsions, syrups, elixirs, etc. or may be presented as a dry product, for reconstitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats, emulsifying agents, for example, lecithin, sorbitan monooleate or acacia; non-aqueous vehicles which may include edible oils, for example, almond oil, fractionated coconut oil, oily esters, propylene glycol, or ethyl alcohol; preservatives, for example, methyl or propyl p-hydroxybenzoates or sorbic acid. Suppositories will contain conventional suppository bases, e.g. cocoa butter or other glyceride.

The composition may also be prepared in suitable forms for absorption through the mucous membranes of the nose and throat or bronchial tissues and may conveniently take the form of powder or liquid sprays or inhalants, lozenges, throat paints etc. For medication of the eyes or ears, the preparations may be presented as individual capsules, in liquid or semi-liquid form, or may be used as drops etc. Topical applications (3.78g.) in water (100 ml.) at 0°–5° and the mixture was stirred at room temperature for 18 hr. The mixture was acidified with 2N hydrochloric acid to pH 2.0 and extracted with ethyl acetate. The combined extracts were washed with water, dried and concentrated to give a solid (9.75 g.). Recrystallisation from petroleum (b.p. 60–80°) gave the title compound (4.0 g., 44%), m.p. 106°–107°, $\lambda_{max}$.(EtOH) 290 nm ($\epsilon$ 11,600), $\tau$ (CDCl$_3$) values include 2.46, 2.66, 2.98 (d doublets, thienyl protons), 8.60 (C(CH$_3$)$_3$).

PREPARATION 4

2-Ethoxyiminophenylacetic acids (syn and anti isomers)

Ethoxamine hydrochloride (4.0 g.) and phenylglyoxylic acid (6.0 g.) were dissolved in water (50 ml.), and the resulting solution was basified to pH 4.5, and stirred at this pH for 15 hr. Acidification and extraction of the mixture gave, after evaporation of the ethyl acetate, a mixture of syn and anti ethoxyiminophenylacetic acids (7.4 g., 94%). Four recrystallisations from cyclohexane failed to give the pure syn acid. However, evaporation of the mother-liquors from the first crystallisation, and recrystallisation of the residue from cyclohexane gave anti-ethoxyiminophenylacetic acid (1.36 g., 17%), m.p. 90.9°–91.6°,$\lambda_{max}$. (ethanol) 249 nm ($\epsilon$ 7,600), $\tau$ (DMSO-d$_6$) values include 2.52 (s, Ph) 5.74 (q, CH$_2$), 8.76 (t, —CH$_3$).

A solution of the mixed acids (4.0 g.) in ether (100 ml.) was treated with an ethereal solution of diazomethane until a yellow colour persisted. Acetic acid was added to destroy excess diazomethane and the ether solution was washed with sodium bicarbonate solution, water, and brine, then dried. Evaporation of the ether gave the methyl esters (4.1 g.) as an orange oil. These were separated on five 40 × 20 cm. preparative plates, eluting with petroleum spirit (b.p. 40°–60°)/ether (3:1). The slower band was eluted with chloroform, and removal of the solvent gave anti-methyl 2-ethoxyiminophenylacetate (1.45 g.) as a pale-yellow oil; $\tau$ (CDCl$_3$) values include 2.58 (Ph), 5.66 (q, CH$_2$), 6.12 (s, OCH$_3$), 8.72 (t, CH$_3$). Similar treatment of the faster band gave syn-methyl 2-ethoxyiminophenylacetate (2.45 g.) as a pale yellow oil, $\tau$ (CDCl$_3$) values include 2.3–2.7 (m, Ph) 5.72 (q, CH$_2$), 6.06 (s, OCH$_3$), 8.67 (t, CH$_3$).

The above syn-methyl ester (2.39 g.) in methanol (60 ml.) was treated with sodium hydroxide solution (2N; 12 ml.), and the solution was stirred for 18 hr. The methanol was removed, and the aqueous mixture, after being acidified to pH 1.5, was extracted with ethyl acetate. The washed and dried extracts were evaporated to dryness, and the residue was recrystallised from cyclohexane to give syn-2-ethoxyiminophenylacetic acid (836 mg.), m.p. 77.9°–79.0°, $\lambda_{max}$. (ethanol) 256.5 nm ($\epsilon$ 12,800); $\tau$ (DMSO-d$_6$) values include 2.48 (m, Ph), 5.74 (q, CH$_2$), 8.71 (t, CH$_3$).

PREPARATIONS 5–29

2-Alkoxyiminoarylacetic Acids

General Procedures

A mixture of the substituted glyoxylic acid and an excess (10 to 15%) of the alkoxyamine hydrochloride was suspended in water or aqueous ethanol, stirred, and the pH of the mixture adjusted to between 4 and 5 (Method B) with sodium hydroxide solution (N to 10N). A clear solution at pH 4 to 5 was maintained during the reaction by further additions of sodium hydroxide solution and ethanol as needed. The reaction mixture was kept at room temperature until all of the ketoacid was consumed (it may be necessary to add a further portion of the more volatile alkoxyamines). The progress of the reaction was followed by acidification of an aliquot, extraction with ethyl acetate and thin layer chromatography of the extract on silica plates (developed with a mixture of chloroform; methanol: acetic acid; 18:2:1). The alkoxyiminoacetic acids were less polar than the starting keto-acids. The reaction times were 2 hr. to 2 days. Reactions carried out at pH 7–8 are designated Method A. When reaction was complete the pH of the mixture was adjusted to between 7 and 8 and the ethanol (if any) was removed by evaporation. The aqueous mixture was extracted with ether, the extract discarded and the aqueous phase acidified to pH < 2 with dilute hydrochloric acid. The mixture was extracted with ethyl acetate, the extract dried and evaporated to give the crude product which was purified by one of the following methods:

a. Crystallisation and recrystallisation (if needed) from a suitable solvent, b. The crude product dissolved in ether was treated with a small excess of a solution of diazomethane in ether. The excess reagent was destroyed with acetic acid and the solution washed with sodium bicarbonate solution and evaporated to give the crude methyl esters. The esters were separated by preparative thick layer chromatography or column chromatography on silica, and then hydrolysed conventionally with alkali to give the pure syn or anti acids, c. The mixture of methyl esters was prepared as in b. and the isomers separated by crystallisation from a suitable solvent and similarly hydrolysed.

These methods were employed to prepare the intermediates listed in Tables 1 (syn-isomers) and 2 (anti-isomers).

TABLE I $$\begin{array}{c} R \diagdown \phantom{xx} \diagup CO_2H \\ \| \\ N \\ \diagdown \\ OR'' \end{array}$$

| Preparation No. | R | R'' | Method | Purification | Mp. ° | $\tau$ values R | (solvent) R'' | $\lambda$max. nm (EtOH) | $\epsilon$ | Yield % (before purification |
|---|---|---|---|---|---|---|---|---|---|---|
| 5 | Ph | C(CH$_3$)$_3$ | A | (a) | 127–129° | 2.2–2.7 (DMSO-d$_6$) | 8.62 | 257 | 13,060 | 100 |
| 6 | Ph | CH$_2$Ph | A | (a) | 103.3° | 2.2–2.7 (CDCl$_3$) | 4.67 (CH$_2$) | 257 | 15,150 | 100 |
| 7 | Ph | CH$_2$–(thien-2-yl) | B | (a) | 110–111° | 2.44 (DMSO-d$_6$) | 4.58 (CH$_2$) 2.92,2.78,2.44 (thien-2-yl) | — | — | — | may be formulated in hydrophobic or hydrophilic bases as ointments, creams, lotions, paints, powders etc.

For veterinary medicine the composition, may, for example, be formulated as an intramammary preparation in either long acting or quick-release bases.

The compositions may contain from 0.1% upwards, preferably from 10–60% of the active material, depending on the method of administration. Where the compositions comprise dosage units, each unit will preferably contain 50–500 mg. of the active ingredient. The dosage as employed for adult human treatment will preferably range from 100–3000 mg. for instance 1500 mg per day, depending on the route and frequency of administration.

The compounds according to the invention may be administered in combination with other therapeutic agents such as antibiotics, for example cephalosporins, other penicillins or tetracyclines.

The following examples illustrate the invention. All temperatures are in °C.

PREPARATION 1.

2-Methoxyiminophenylacetic acids (syn and anti isomers).

A solution of sodium (5 g.) in dry methanol (100 ml) was added to a solution of 0-methylhydroxylamine hydrochloride (15 g.) in dry methanol (100 ml) until neutral to phenolphthalein. The precipitated sodium chloride was removed by filtration, and the filtrate added to a solution of phenylglyoxylic acid (25 g.) in dry methanol (100 ml). The solution was refluxed for 2 hours, cooled, and evaporated to an oil, which was dissolved in ether (200 ml), refiltered and evaporated to an oil (32.9 g.). This was crystallised from petroleum spirit, (bp. 60–80°) producing a white solid (19.61 g.) and oil (3.9 g.).

The solid (17.8 g.) and the oil (3.9 g.) were combined (21.7 g.) and methylated with ethereal diazomethane, producing an oil (24.2 g.). This was purified by chromatography on silica gel (600 g.), producing syn-methyl 2-methoxyiminophenylacetate as an oil (13.6 g. 55%), $\lambda_{max.}$ (EtOH) 259 nm ($\epsilon$ 10,400) and anti-methyl 2-methoxyiminophenylacetate, the slower component, as a solid (8.7 g.; 35%), m.p. 54°, $\lambda_{max.}$ (EtOH) 251 nm ($\epsilon$ 7,260).

Methyl 2-methoxyiminophenylacetate (anti-isomer) (8.7 g.) was dissolved in methanol (100 ml) and 2N sodium hydroxide solution (22 ml.) was added. The solution was stirred at room temperature for 1 hour, and the pH adjusted to 7 with 2N-hydrochloric acid. Methanol was removed by evaporation, water (150 ml.) was added, and the solution acidified to pH 1.5 with 2N-hydrochloric acid. The mixture was extracted with ethyl acetate (3 × 100 ml), the organic extracts were combined, dried and evaporated to give a solid (6.74 g.) which was crystallised from petroleum spirit (bpt. 60–80°): benzene, producing anti-2-methoxyiminophenylacetic acid (4.84 g.), m.p. 103–104°, $\lambda_{max.}$ (EtOH) 248 nm ($\epsilon$ 7,010). $\tau$ (CDCl$_3$) values include 2.64 (Ph), 5.92 (CH$_3$).

Methyl 2-methoxyiminophenylacetate (syn-isomer) (13.6 g.) was hydrolysed in a similar manner, but the hydrolysis mixture was stirred for 40 hours at room temperature. The white solid (11.13 g.) formed was crystallised from petroleum spirit (b.p. 60°–80°); benzene producing syn-2-methoxyiminophenylacetic acid as a white solid (10.02 g.). m.p. 96°–97°, $\lambda_{max.}$ (EtOH) 255 nm, ($\epsilon$ 13,200), $\tau$ (CDCl$_3$) values include 2.2–2.8 (Ph), 5.92 (CH$_3$).

PREPARATION 2

2-Methoxyimino-(thien-2-yl)-acetic acids (syn and anti isomers)

A solution of methoxyamine hydrochloride (5.85 g.) in dry methanol (60 ml.) was neutralised (phenolphthalein) with a solution of sodium methoxide in methanol [from sodium (2.5 g.) and dry methanol (50 ml.)]. The precipitated sodium chloride was removed by filtration, and the filtrate was added to a solution of thien-2-ylglyoxylic acid (10 g.) in dry methanol (60 ml.). The resulting solution was refluxed for 1 hour, cooled, and evaporated to an oil. Ether (100 ml.) was added, the mixture was filtered, and the filtrate was evaporated to an oil (13.06 g.).

The oil (12.5 g.) was dissolved in ether (50 ml.) and an ethereal solution of diazomethane was added until a permanent yellow colour remained. The excess diazomethane was destroyed by leaving the solution in sunlight for 1 hour. Evaporation of this solution produced an oil (13.2 g.).

The oil (10.33 g.) was purified by preparative plate chromatography (Kieselgel PF$_{254 + 366}$) developing three times with 75% petroleum spirit (b.p. 60°–80°) in benzene, producing a. methyl 2-methoxyimino-2-(thien-2-yl)-acetate (syn isomer)
(3.44 g., 27%), $\lambda_{max.}^{EtOH}$ 290 nm ($\epsilon$ 11,250), $\lambda_{inf.}$ 271 nm ($\epsilon$ 5,400) $\nu_{max.}$ (CHBr$_3$) 1738 and 1230 cm$^{-1}$ (CO$_2$Me). $\tau$ values (CDCl$_3$) include 6.06 (s, CO$_2$Me), 5.78 (s, OCH$_3$); and b. methyl 2-methoxyimino-2-(thien-2-yl)-acetate (anti-isomer)
(1.21 g., 9.5%), $\lambda_{max.}^{EtOH}$ 221 and 288 nm ($\epsilon$ 5,020 and 11,000). $\nu_{max.}$ (CHBr$_3$) 1732 and 1212 cm$^{-1}$ (CO$_2$Me), $\tau$ (CDCl$_3$) values include 6.06 (s, CO$_2$Me), 6.00 (s, OCH$_3$) and further fractions which were isomeric mixtures.

2N-Sodium hydroxide (8.27 ml.) was added to a solution of methyl 2-methoxyimino-2-(thien-2-yl)-acetate (syn-isomer) (3.28 g.) in methanol (50 ml.) and the solution was stirred at room temperature for 18 hours. Water (20 ml.) was added and the solution was evaporated to remove methanol, and then washed with ethyl acetate. The pH of the solution under ethyl acetate (50 ml.) was altered to 2 with 2N-hydrochloric acid. The layers were separated and the aqueous phase was extracted with ethyl acetate. The organic extracts were combined, dried, and evaporated to a white solid (2.58 g.). This was crystallised from cyclohexane, producing the title compound (syn-isomer) (2.23 g., 73%), m.p. 105.5°, $\lambda_{max.}^{EtOH}$ 289 nm ($\epsilon$ 10,100), $\lambda_{inf.}$ 262 and 271 nm. ($\epsilon$ 7,750 and 8,150), $\tau$ (CDCl$_3$) values include 0.32 (OH) and 5.92 (OCH$_3$). Similar hydrolysis of the anti-methyl ester gave 2-methoxyimino-(thien-2-yl)-acetic acid (anti-isomer) (0.85 g.), $\lambda_{max.}^{EtOH}$ 286–287 nm ($\epsilon$ 10,200), $\tau$ (CDCl$_3$) values include 1.31 (OH) and 5.73 (OCH$_3$).

PREPARATION 3

2-t-Butoxyiminothien-2-ylacetic acid (syn isomer)

A solution of thien-2-ylglyoxylic acid (6.2g.) and sodium bicarbonate (3.36g.) in water (100 ml.) was added dropwise to a stirred solution of t-butoxyamine hydrochloride (5.65 g.) and sodium bicarbonate TABLE I-continued $$R\underset{\underset{OR''}{N}}{\overset{CO_2H}{\|}}$$

| Preparation No. | R | R'' | Method | Purification | Mp. ° | τ values R | (solvent) R'' | λmax. nm (EtOH) | ε | Yield % (before purification) |
|---|---|---|---|---|---|---|---|---|---|---|
| 8 | (thienyl) | $CH_3$ | B | (a) | 108–109° | 2.61–2.91 ($CDCl_3$) | 5.92 | 289 | 10,700 | 91 |
| 9 | (thienyl) | $C_2H_5$ | B | (a) | 89.5–91.5° | 2.29, 2.76 2.86 (DMSO-$d_6$) | 5.79 ($CH_2$) 8.72 ($CH_3$) | 289.5 | 12,500 | 87 |

$$R\underset{\underset{OR''}{N}}{\overset{CO_2H}{\|}}$$

| Preparation No. | R | R'' | Method | Purification | Mp. ° | τ values R | (DMSO-$d_6$) R'' | λmax. nm (EtOH) | ε | Yield % (before purification) |
|---|---|---|---|---|---|---|---|---|---|---|
| 10 | (thienyl) | $CH_2Ph$ | B | (a) | 114–115° | 2.29, 2.73, 2.84 (DMSO-$d_6$) | 2.59 (Ph) 4.77 ($CH_2$) | 290 | 12,300 | 88 |
| 11 | (thienyl) | $CH_2CH_2Br$ | B CH | (b) | 92.6° | 2.23; 2.71; 2.83 | 5.54; 6.28 | 289 | 12,200 | 77 |
| 12 | (chloronaphthyl) | $CH_3$ | B | (b) | 104° | — | — | — | — | 93 |
| 13 | (naphthyl) | $CH_3$ | B | (b) | 98–99° | 1.38 1.8–2.1 2.1–2.5 | 5.9 | 294.5 | 8,100 | 96 |
| 14 | (naphthyl) | $C(CH_3)_3$ | A | (b) | 122–123° | 1.3–1.5 1.3–2.1 2.2–2.5 | 8.62 | 296.5 | 9,300 | 96 |
| 15 | (naphthyl) | $CH_2Ph$ | A | (a) | — | 1.53, 1.92, 2.2–2.7 | 2.50 (Ph) 4.64 ($CH_2$) | 294 | 8,300 | 86 |
| 16 | (furyl) | $CH_3$ | B | (a) | 85–87° | 2.10, 3.18, 3.33 | 6.06 | 275 | 21,500 | 81 |
| 17 | (furyl) | $C(CH_3)_3$ | B | (a) | 110.5–111.5° | 2.12, 3.24, 3.35 | 8.70 | 275.5 | 16,040 | 95 |
| 18 | (furyl) | $CH_2Ph$ | B | (a) | 104–105.5° | 2.12, 3.19, 3.33 | 2.58 (Ph) 4.75 ($CH_2$) | 277 | 17,650 | 81 |
| 19 | (benzothienyl) | $CH_3$ | B | (c) | 129–130° | 1.40, 1.83, 1.95, 2.44 | 5.92 | 233 284 296.5 306.5 | 22,900 10,900 10,500 9,270 | 99 |
| 20 | (benzothienyl) | $C(CH_3)_3$ | B | (a) | 175–176° | 1.88, 2.03, 2.3–2.7 | 8.6 | 234 284.5 297 307.5 | 21,900 11,200 10,800 9,400 | 93 |
| 21 | (benzothienyl) | $CH_3$ | B | (a) | 143–144° (dec) | 2.00, 2.36, 2.55 | 6.00 | 231 252.5 296.5 | 5,400 7,300 23,600 | 98 |
| 22 | (furyl) | $CH_2$-(furyl) | B | (a) | 104.8–105.4° | 2.17, 3.25, 3.40 | 4.92 ($CH_2$) 2.33; 3.5 furyl protons) | 276 | 16,300 | 97 |

TABLE I-continued $$\underset{\underset{OR''}{\overset{\|}{N}}}{R}\diagdown \overset{CO_2H}{\diagup}$$

| Preparation No. | R | R'' | Method | Purification | Mp. ° | τ values R | τ values R'' | (DMSO-d₆) | λmax. nm (EtOH) | ε | Yield % (before purification) |
|---|---|---|---|---|---|---|---|---|---|---|---|
| 23 | (furyl) | CH₂-(thienyl) | B | (a) | 110–111° | 2.12;3.20; 3.36 | 4.66 (CH₂) 2.43; 2.83; 2.98 thienyl protons | | 234.5 277 | 11,200 17,500 | 90 |
| 24 | (furyl) | C₂H₅ | B | (a) | 91–92° | 2.10;3.19; 3.33 | 5.79; 8.75 | | 274.5 | 15,800 | 92 |

TABLE 2

$$\underset{\underset{R''O}{\overset{\|}{N}}}{R}\diagdown \overset{CO_2H}{\diagup}$$

| Preparation No. | R | R'' | Method | Purification | Mp. ° | τ values R | τ values R'' | (DMSO-d₆) | λmax. nm (EtOH) | ε | Yield % (before purification) |
|---|---|---|---|---|---|---|---|---|---|---|---|
| 25 | 2-Cl-C₆H₄ | CH₃ | B | (c) | 110.5–111° | 2.35–2.65 | 6.02 | | 225 (infl.) | 8,370 | 93 |
| 26 | 2-Cl-C₆H₄ | C(CH₃)₃ | B | (a) | 125–126.5 | 2.35–2.90 | 8.72 | | 228 (infl) | 9,080 | 93 |
| 27 | 2-Cl-C₆H₄ | CH₂Ph | B | (a) | 116° | 2.30–2.80 | 2.63 (Ph) 4.70 (CH₂) | | 228 (infl.) | 9,900 | 98 |
| 28 | naphthyl | CH₃ | B | (a),(c) | 131° | 1.8–2.1 2.2–2.7 | 6.06 | | 269 279.5 | 5,400 6,800 | 96 |
| 29 | naphthyl | CH₂Ph | A | (a) | 128° | 1.9–2.2 2.2–2.6 | 2.70 (Ph) 4.77 (CH₂) | | 268.5 279.5 | 5,900 6,000 | 86 |

PREPARATION 30

2-Benzyloxyiminophenylacetic Acid (anti-isomer)

Oxalyl chloride (3.75 ml.) was added to a magnetically stirred suspension of syn-2-benzyloxyiminophenylacetic acid (10.2 g.) in dry benzene (100 ml.). Dimethylformamide (2 drops) was added and the mixture stirred for 2½ hr., the solid dissolved in about ½ hr. The reaction mixture was evaporated and the residue dissolved in dry benzene (100 ml.). A mixture of dry methanol (20 ml.) and dry pyridine (8.0 ml.) was added and the mixture stirred for 1½ hr. The solvents were evaporated and a solution of the residue in ether was washed with dilute hydrochloric acid, water, dilute sodium bicarbonate solution and water. Evaporation of the dried ether solution gave a mixture of syn- and anti-methyl 2-benzyloxyiminophenylacetates (10.9 g., 100%) in the ration of 45:55.

A solution of the mixture of methyl esters (2.7 g) in methanol (ea. 80 ml.) was treated with tetrabutylammonium hydroxide (6.5 ml; 40%) and then made up to 100 ml. with methanol. At intervals 3 ml. aliquots of the reaction mixture were removed and titrated against 0.1N hydrochloric acid. After 4 hr. the hydrolysis was about 45% complete and 1.0 N hydrochloric acid (4.7 ml; the calculated amount to neutralise the remaining 85% of the reaction mixture) was added. Water was added and the reaction mixture evaporated under reduced pressure to remove methanol. The mixture was extracted with ethyl acetate and the organic extract washed thoroughly with dilute hydrochloric acid and then worked up conventionally for acidic and neutral products. The liquid, neutral ester fraction, (1.15 g; 50%), was estimated to contain about 80% syn and 20% anti isomers by N.M.R. The acidic fraction was a solid (0.91 g; 42%) m.p. 93.0° which was crystallised from cyclohexane containing a little benzene to give pure anti-2-benzyloxyiminophenylacetic acid m.p. 96.0° [a mixture with authentic syn acid (m.p. 103°) melted at 77.8°], $\lambda_{max.}$ (EtOH) 250.5 nm (ε9,100), τ (DMSO-d₆) values include 2.44 (m, Ph), 2.62 (s, CH₂Ph), 4.73 (s, CH₂).

PREPARATION 31 a. Methyl 2-(1-ethoxy)ethoxyimino-2-(thien-2-yl)acetate (syn-isomer)

To a stirred mixture of methyl 2-hydroxyimino-2-(thien-2-yl)acetate syn-isomer (3.98 g.) and ethyl vinyl ether (2.5 mls) in ethyl acetate (25 mls) was added phosphorous oxychloride (2 drops). After 20 mins. at 50° the ethyl acetate was washed with saturated sodium bicarbonate solution, dried over sodium sulphate and evaporated to an oil, giving methyl 2-(1-ethoxy) ethoxyimino-2-(thien-2-yl)acetate (syn-isomer) (5.7 g; 100%) $\lambda_{max}$. (EtOH) 289 nm ($\epsilon$ 11,700), $\tau$ (CDCl$_3$; 60 MHz) 2.61 (multiplet; thienyl H$_5$), 2.82 to 2.97 (multiplet; thienyl H$_3$ and H$_4$), 4.64 (quartet, J5Hz;

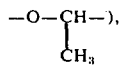

6.06 (singlet, —COOCH$_3$), 6.24 (quartet, J 7 Hz, OCH$_2$), 8.56 (doublet J 5 Hz; CH—CH$_3$), 8.79 (triplet, J 7 Hz; O.CH$_2$CH$_3$).

b. 2-(1-Ethoxy)ethoxyimino-2-(thien-2-yl)acetic acid sodium salt (syn-isomer)

1N-Sodium hydroxide (1 equiv.) and enough methanol to form a homogeneous system were added to methyl 2-(1-ethoxy)ethoxyimino-2-(thien-2-yl)acetate (syn-isomer) (5.7 g.). After 4 hrs. at 50° the methanol was evaporated and the residue azeotroped with benzene/methanol giving a white solid, 2-(1-ethoxy)ethoxyimino-2-(thien-2-yl)acetic acid sodium salt(syn-isomer) (4.6 g, 78.5%),$\lambda_{max}$. (pH 6 buffer) 287.5 nm ($\epsilon$ 10,650), $\tau$ (D$_2$O) values include 2.42 (multiplet; thienyl H$_5$), 2.68 to 2.84 (multiplet; thienyl H$_3$ and H$_4$), 4.63 (quartet, J 5 Hz;

6.21 (quartet, J 7 Hz; —CH$_2$—CH$_3$), 8.57 (doublet, J 5 Hz;

8.82 (triplet, J 7 Hz; —CH$_2$—CH$_3$).

PREPARATION 32 syn-Then-2-yloxyimino(thien-2-yl)acetic acid

Then-2-yloxamine hydrochloride (7.37 g.) and thien-2-ylglyoxylic acid (6.24 g.) were dissolved in ethanol (110 ml.) and water (20 ml.). The pH of the solution was adjusted to 5.0, and this solution was stirred for 22 hr. The ethanol was evaporated off, and the aqueous mixture was neutralised, washed twice with ether, then acidified to pH 1.5. The acid mixture was extracted with ethyl acetate. The combined extracts were washed, dried and evaporated to dryness to give a yellow oil (9.2 g., 86%) which crystallised on standing. TLC indicated the solid to be a mixture of isomers. Recrystallisation of this solid several times from cyclohexane effected no separation of isomers. The mixture of acids (5.0 g.) was esterified with diazomethane to give the mixture of methyl esters, as a pale-yellow oil.

To a solution of the mixture of methyl esters (2.14 g.) in methanol (50 ml.) was added 2N sodium hydroxide solution (7.6 ml.). After stirring this solution for 0.5 hr., the solution was neutralised. The methanol was evaporated and the aqueous residue was extracted with ethyl acetate. The extracts were washed, dried, and evaporated to dryness to give a yellow oil (1.0 g.). This oil was dissolved in methanol (25 ml.) and stirred for 18 hr. with 2N sodium hydroxide solution (5 ml.). Methanol was removed by evaporation and the aqueous residue, after washing with ethyl acetate then acidification to pH 1.7, was extracted with ethyl acetate. The extracts were washed, dried, and evaporated to dryness to give a solid (730 mg.). Recrystallisation of this solid twice from cyclohexane gave syn-2-(thien-2-ylmethyl)oxyimino(thien-2-yl)acetic acid (369 mg.), m.p. 101°–102°, $\lambda_{max}$. (EtOH) 239, 289.5 nm ($\epsilon$ 11,700, 12,300), $\tau$ (DMSO-d$_6$) values include 4.67 (s, CH$_2$).

PREPARATION 33 syn-2-Benzyloxyiminobenzo-[b]-thien-2'-ylacetic acid

Benzo[b]-thien-2-ylglyoxylic acid (3.092 g) and benzyloxyamine hydrochloride (2.72 g.) in ethanol (170 ml.) and water (70 ml.) were adjusted to pH 4.5 with sodium hydroxide (40%). The solution was stirred at this pH at room temperature for 6 hr. Benzyloxyamine hydrochloride (500 mg.,) was added and the solution stood at room temperature overnight. The solution was adjusted to pH 8 and washed with ether. The aqueous phase was acidified under ether to pH 1.5. The ether layer was washed with water and dried. Evaporation gave a cream coloured solid (4.28 g, 91%) as an isomeric mixture.

The crude isomeric mixture was treated in ether with excess diazomethane in ether at 0°–5°. The excess reagent was destroyed with acetic acid and the ether solution was washed with sodium bicarbonate, water and dried. Evaporation gave an oil (4.45 g., 91%). This was dissolved in methanol (140 ml.) and treated at room temperature with sodium hydroxide solution (1N; 14 ml.) for 2¼ hr. Hydrochloric acid (2N, 7 ml.) was added and the alcohol was removed by evaporation. The aqueous phase was partitioned between sodium bicarbonate solution and ether. The ether layer was washed with water and dried, evaporation gave an oil (2.16 g., 44%). This was hydrolysed directly in refluxing methanol (70 ml.) with sodium hydroxide (1N; 7 ml) for 4 hr. The methanol was removed by evaporation and the residue partitioned between water and a little ether. The aqueous layer was acidified under ether to pH 1.5 and the ether layer was washed with water, dried and evaporated to give a pale cream solid (1.97 g, 42%). Crystallisation from a mixture of benzene and cyclohexane gave the title compound as a white crystalline solid, (1.61 g; 35%), m.p. 141°–143° (dec.),$\lambda_{max}$. (EtOH) 230.5, 253, 297.5 nm ($\epsilon$ 16,400; 7,400; 24,100), $\tau$ (DMSO-d$_6$) values include 2.00, 2.36, 2.55 (aromatic protons), 4.71 (CH$_2$ singlet).

PREPARATION 34

2-Phenoxyimino(thien-2-yl)acetic acid (anti-isomer)

Diphenyliodonium bromide (1.74 g.) was added to a solution of methyl 2-hydroxyimino-thien-2'-ylacetate sodium salt (anti-isomer) (prepared by treating methyl anti-hydroxyimino-thien-2-ylacetate and 1 equivalent sodium methoxide) (1.04 g.) in benzene:dimethylformamide (2:1, 30 ml.) and the mixture was stirred at room temperature for 30 min. then poured into water. The aqueous solution was extracted with ethyl acetate washed with water, dried and evaporated to give the anti methyl ester (1.9 g) as a yellow oil.

2N-Sodium hydroxide (7.3 ml) was added to a solution of the anti methyl ester (1.9 g.) in methanol (20 ml.) and the mixture was left at room temperature for 30 min. The methanol was removed by evaporation, the aqueous residue was diluted with water, washed with ethyl acetate and acidified to pH 2.0 with 2N-hydrochloric acid in the presence of ethyl acetate. The organic fraction was separated and combined with the ethyl acetate extracts of the aqueous fraction, washed with water, dried and evaporated to give pale yellow crystals. Recrystallisation from benzene/cyclohexane gave the title compound (830 mg, 46%) as yellow needles, m.p. 86°, $\lambda_{max}$. (EtOH), 297 nm ($\epsilon$ 12,100), $\lambda$ infl. 275 nm ($\epsilon$ 9,750), $\tau$ values (DMSO-$d_6$) include 1.89, 2.02, 2.69 (thien-2-yl protons) 2.80 and 3.1–3.4 (Ph).

PREPARATION 35

Benzo[b]-thien-2-ylglyoxylic acid and Benzo[b]-thien-3-ylglyoxylic acid

A mixture of 2- and 3-acetylbenzo[b]-thiophene (ca. 1:1) (11.0 g.) in pyridine (80 ml.) was warmed to 60° with vigorous stirring and selenium dioxide (9.92 g.) was added portionwise. The mixture was heated to 110°C and an exothermic reaction occured, the temperature rising to 120°. The reaction was stirred at 90° for 45 mins. and then left to cool. Water (80 ml.) was added and the mixture filtered through a kieselguhr pad. The pyridine was removed by evaporation and the aqueous residue again filtered. The filtrate was acidified to pH 2 under ether with 40% orthophosphoric acid (40 ml).

The aqueous phase was extracted with ether and the ether fractions were combined, washed with water and dried. Evaporation gave an orange crystalline solid (11.0 g., 86%). Crystallisation from benzene (100 ml) gave bright yellow crystals of benzo[b]-thien-2-ylglyoxylic acid (2.3 g. 18%), m.p. 175.9°, $\lambda_{max}$. (EtOH), 233, 247, $\lambda$ infl. 308 nm. ($\epsilon$ 11,400; 7,200; 14,600), $\tau$ (DMSO-$d_6$) values include 1.83 (C-4 and C-7 protons), 1.42 (C-3 proton), 2.40 (C-5 and C-6 protons).

The mother liquor was concentrated to an orange oil which crystallised on standing (8 g.). Recrystallisation from benzene (20 ml.) gave pale yellow needles of benzo-[b]-thien-3-ylglyoxylic acid (1.6 g., 12.5%), m.p. 92°–93°, $\tau$ (DMSO-$d_6$) values include 0.83 (C-2 proton), 1.32 (C-4 proton), 1.79 (C-7 proton), 2.40 (C-5 and C-6 protons), $\lambda_{max}$. (EtOH) 235, 310.5 nm ($\epsilon$ 11,200 and 7,400).

2-Alkoxyiminoarylacetyl Chlorides

PREPARATION 36 syn-2-Methoxyiminophenylacetyl chloride

Phosphorous pentachloride (5.21 g) was added in portions to a stirred suspension of syn-2-methoxyiminophenylacetic acid (4.51 g.) in dry benzene (20 ml.). Thionyl chloride (0.3 ml) was added to the solution, which was refluxed for 30 minutes. Benzene was removed by evaporation, and the residue distilled, producing a mixture of syn- and anti- acid chlorides (ca. 1:1) as a colourless oil (3.08 g., 62%), b.p. 74° (0.01 mm). A repeat of this reaction (on 5.04 mmole) at room temperature also produced a mixture of the isomeric acid chlorides.

The acid chlorides were separated and purified by preparative plate chromatography, developing three times with petroleum spirit (b.p. 60°–80°) producing the title compound as a colourless oil (1.43 g. 24%).

In a further experiment a mixture of syn- and anti-2-methoxyiminophenylacetic acids (10 g., ca 1:1) were converted to a mixture of acid chlorides as above and chromatographed on silica gel (120 g., Hopkins and Williams, MFC) using petroleum spirit (b.p. 60°–80°) to give syn-2-methoxyiminophenylacetyl chloride (4.32 g., 39%).

General Method for Converting a 2-Alkoxyiminoarylacetic Acid into its Acid Chloride without Isomerisation A solution of the pure syn- or anti- 2-alkoxyiminoarylacetic acid (1 equiv.) in methanol (ca. 2–4 ml./mmole.) was treated with sodium methoxide (1 equiv.) in methanol at 0°–25° and the mixture evaporated to give the sodium salt which may be dried by azeotroping with several portions of benzene and/or drying in vacuo over phosphorus pentoxide.

The anhydrous sodium salt (1 equiv.) was suspended in dry benzene (ca. 5 ml/mmole) containing a few drops of dry dimethylformamide and treated with freshly distilled oxalyl chloride (1–2.5 equiv.). The mixture was stirred at room temperature for 1 hr. and then evaporated to remove benzene. The resulting acid chlorides were not characterised but were dissolved in acetone or methylene chloride and used immediately to acylate the appropriate penicillin nucleus.

The following acids were converted into their acid chlorides in this way:
Syn-2-EThoxyiminophenylacetic acid,
Syn-2-t-Butoxyiminophenylacetic acid,
Syn-2-Benzyloxyiminophenylacetic acid,
Syn-2-Then-2'-yloxyiminophenylacetic acid,
Syn-2-Methoxyimino-(thien-2-yl)acetic acid,
Syn-2-Ethoxyimino-(thien-2-yl)acetic acid,
Syn-2-t-Butoxyimino-(thien-2-yl)acetic acid,
Syn-2-(2-Bromoethoxy)imino-(thien-2-yl)-acetic acid,
Syn-2-Benzyloxyimino-(thien-2-yl)acetic acid,
Syn-2-Then-2'-yloxyimino-(thien-2-yl)-acetic acid,
Syn-2-(1-Ethoxy)ethoxyimino-(thien-2-yl)-acetic acid,
Syn-2-Methoxyimino-o-chlorophenylacetic acid,
Syn-2-Methoxyiminonaphth-1'-ylacetic acid,
Syn-2-t-Butoxyiminonaphth-1'-ylacetic acid,
Syn-2-Benzyloxyiminonaphth-1'-ylacetic acid,
Syn-2-Methoxyiminobenzo-[b]-thien-3'-ylacetic acid,
Syn-2-t-Butoxyiminobenzo-[b]-thien-3'-ylacetic acid,
Syn-2-Methoxyiminobenzo-[b]-thien-2'-ylacetic acid,
Syn-2-Benzyloxyiminobenzo-[b]-thien-2'-ylacetic acid,
Syn-2-Methoxyimino(fur-2-yl)acetic acid,
Syn-2-t-Butoxyimino-(fur-2-yl)acetic acid,
Syn-2-Furfuryloxyimino-(fur-2-yl)acetic acid,
Syn-2-Thien-2'-yloxyimino-(fur-2-yl)acetic acid,
Syn-2-Ethoxyimino-(fur-2-yl)acetic acid
Syn-2-Benzyloxyimino-(fur-2-yl)acetic acid; and
Anti-2-Methoxyiminophenylacetic acid,
Anti-2-Ethoxyiminophenylacetic acid,
Anti-2-Benzyloxyiminophenylacetic acid,
Anti-2-Phenoxyimino-(thien-2-yl)acetic acid,
Anti-2-Methoxyimino-o-chlorophenylacetic acid,
Anti-2-t-Butoxyimino-o-chlorophenylacetic acid,
Anti-2-Benzyloxyimino-o-chlorophenylacetic acid,
Anti-2-Methoxyiminonaphth-1'-ylacetic acid, and
Anti-2-Benzyloxyiminonaphth-1'-ylacetic acid.

PREPARATION A

Then-2-yloxamine hydrochloride (used as a starting material in Preparation 7)

a. N-(Then-2-yloxy)phthalimide

Anhydrous potassium carbonate (11.04 g.) was added to a stirred suspension of N-hydroxyphthalimide (17.12 g.) in dry dimethyl sulphoxide (200 ml.). A brown colour developed, 2-Chloromethylthiophene (28.5 g.) was added dropwise and the mixture was stirred for 16 hr., during which time the colour disappeared. The suspension was poured into water (800 ml.) and cooled to 5°. The white precipitate was filtered off, and recrystallised from ethanol to give colourless needles of N-(then-2-yloxy)phthalimide (23.4 g., 83%), m.p. 129.7°–130.9° τ values (DMSO-$d_6$) are 4.58 ($CH_2$), 2.28, 2.69, 2.90 (thienyl protons) 2.08 (phthalimide protons)

b. Then-2-yloxamine hydrochloride

A mixture of N-(then-2-yloxy)phthalimide (22.4 g.) 100% hydrazine hydrate (5 g) and ethanol (600 ml.) was heated under reflux for two hours. Initially, a yellow solution was formed, but soon solid began to precipitate. The mixture was cooled, then acidified with concentrated hydrochloric acid (12 ml.). The precipitated phthalhydrazide was filtered off and washed with ethanol (3 × 50 ml.) and water (100 ml.). The combined filtrate and washings were evaporated to dryness, and the residue, suspended in water, was basified with 2N sodium hydroxide solution. The basic mixture was extracted with ether, and the combined extracts were washed (water, saturated brine), dried, and saturated with dry hydrogen chloride. The precipitated solid was collected and well washed with ether to give then-2-yloxamine hydrochloride, (12.45 g., 87%), m.p. 157.1°–157.5°. A sample recrystallised from ethanol/ether had m.p. 161.7°–162.1° τ values (DMSO-$d_6$) include 4.69 ($CH_2$), 2.30, 2.72, 2.90 (thienyl protons).

PREPARATION B

Furfuryloxamine Hydrochloride (used as a starting material in Preparation 22)

a. N-Furfuryloxyphthalimide

To a stirred mixture of N-hydroxyphthalimide (41 g.), anhydrous potassium carbonate (26.4 g.) and dry dimethyl sulphoxide (400 ml.) was added 2-chloromethylfuran (freshly prepared, but undistilled, from 46.2 g. furfuryl alcohol according to the method of W.R. Kirner JACS, 1928, 50, 1955). The mixture was stirred for 18 hr., then poured into water (1.5 l). The precipitated solid was filtered off, washed well with water, and recrystallised from ethanol to give N-furfuryloxyphthalimide (42.8 g., 70%), m.p. 145.3°–146.2° τ values (DMSO-$d_6$) are 4.80 ($CH_2$), 2.22, 3.30, 3.50 (furyl protons) 2.08 (phthalimide protons).

b. Furfuryloxamine Hydrochloride

100% Hydrazine hydrate (20 ml.) was added to a stirred solution of N-furfuryloxyphtyalimide (42.0 g.) in methylene chloride (600 ml.). A copious precipitate formed immediately, and the mixture was stirred for 45 min. 5N Ammonium hydroxide solution (500 ml.) was added to dissolve the precipitate, the two layers were separated, and the aqueous layer was washed twice with methylene chloride. The combined methylene chloride extracts were washed (saturated brine) and dried. Mehtylene chloride was evaporated off, and the residual liquid was dissolved in ether (250 ml.). Dry hydrogen chloride was passed into this solution for 1 hour. The precipitated solid was filtered off, washed with ether, dried, and recrystallised from isopropanol to give furfuryloxamine hydrochloride (12.89 g., 50%), m.p. 135°–136° (decomp) τ values (DMSO-$d_6$) include 4.87 ($CH_2$), 2.20, 3.27, 3.44 (furyl protons).

PREPARATION C

The general procedures described in Preparations 5–29 for the preparation of 2-alkoxyiminoarylacetic acids were employed to prepare the intermediates listed in tabular form below (the Table may be regarded as a continuation of Table 1).

TABLE 2

$$\begin{array}{c} R \diagdown \quad \diagup CO_2H \\ C \\ \| \\ N \\ \diagdown OR'' \end{array}$$

| Preparation No. | R | R'' | Method | Purification | Mp. ° | τ values R | (DMSO-$d_6$) R'' | $\lambda_{max}$ nm (EtOH) | ε | Yield % |
|---|---|---|---|---|---|---|---|---|---|---|
| 37 | Ph | n-$C_4H_9$ | B | (b) | oil | 2.4–2.6 | 5.82, 2.3–2.8, 9.08 | 257 | 11,500 | 100 |
| 38 | (2-thienyl) | —$C_2H_5$ | B | (a) | 74.0° | 2.2–2.4, 2.65 | 5.81, 8.75 | 258.5 | 13,800 | 96 |
| 39 | (benzofuryl) | —$C_2H_5$ | B | (a) | 125.5–126° | 2.1–2.8, 2.75 | 5.69, 8.71 | 228 inf 290 297 307 | 7,200 22,940 24,600 2,500 | 84 |

2-Alkoxyiminoary/acetyl Chlorides (continued)

The following acids were converted into their acid chlorides using the general method for converting a 2-alkoxyimino arylacetic acid into its acid chloride without isomerisation described immediately after preparation 36:

Syn-2-Butoxyiminophenylacetic acid
Syn-2-Isopropoxyiminophenylacetic acid
Syn-2-Ethoxyimino-(benzo[b]-fur-2-yl) acetic acid
Syn-2-Ethoxyimino-(thien-3-yl)acetic acid

PREPARATION 40

2-Phenoxyimino-2-phenylacetic acid (syn- isomer)

A solution of syn-2-hydroxyimino-2-phenylacetic acid (33 g) in dry methanol (500 ml) was treated with 1.105 N sodium methoxide solution (486 ml), and stirred for 15 minutes. To the solution was added diphenyliodonium bromide (90 g), and the resulting mixture was stirred for 18 hours under nitrogen. A small amount of solid was filtered off, and the filtrate was evaporated to dryness. Water (600 ml) and ether (600 ml) were added to the residue, and the pH of the mixture was adjusted to 7.0 with concentrated hydrochloric acid. The aqueous layer was washed twice with ether, and then acidified under ether to pH 1.8 with concentrated hydrochloric acid. The acid mixture was extracted into ether, and the combined extracts were washed (water, saturated brine), dried, and evaporated to give a dark brown solid (ca 35 g). This solid was triturated with ice-cold nitromethane. The solid was collected, washed with a little cold nitromethane, and dried in vacuo to give fawn crystals of the title acid (24.41 g, 51%), m.p. 104.8°–106.1°, $\lambda_{max.}$ (ethanol) 267.5, 285 nm ($\epsilon$ 11,600; 10,100).

Similarly were prepared:

PREPARATION 41

2-Phenoxyimino-2-(thien-2-yl)acetic acid (synisomer) (52%) m.p. 98.3°–99.5°, $\lambda_{max.}$ (ehtanol) 267.5, 303 nm. ($\epsilon$ 9,900; 12,000). and

PREPARATION 42

2-Phenoxyimino-2-(fur-2-yl)acetic acid (synisomer) (34%), m.p. 100.7°–100.9°, $\lambda_{max.}$ (ethanol) 270.5, 292.5 nm ($\epsilon$ 14,300; 15,700).

PREPARTION 43

2-Cyclopentyloxyimino-2-(fur-2-yl)acetic acid (synisomer)

Fur-2-yl glyoxylic acid (2.80 g) and cyclopentyloxamine hydrochloride (3.3 g) were dissolved in a mixture of water (100 ml) and ethanol (50 ml), and the pH of the solution was adjusted to 5.0. The solution was stirred for 19 hours, the alcohol was evaporated off, and the solution was acidified to pH 1.5 under ethyl acetate. The acid mixture was extracted into ethyl acetate, and the combined extracts were washed, dried, and evaporated to give the crude acid (4.38 g). This acid was treated with charcoal in benzene for 15 minutes, filtered, and the filtrate was evaporated to give a solid, which was recrystallised twice from cyclohexane to give the title acid (2.28 g, 51%), m.p. 96.6°–97.7°, $\lambda_{max.}$ (ehtanol) 277.5 nm (15,600).

PREPARATIONS 44–47

2-Alkoxyimino-2-arylacetic acids

General Procedures

A mixture of the substituted glyoxylic acid and an excess (10 to 15%) of the alkoxyamine hydrochloride was suspended in water or aqueous ethanol, stirred, and the pH of the mixture adjusted to between 4 and 5 with sodium hydroxide solution (N to 10N). A clear solution at pH 4 to 5 was maintained during the reaction by further additions of sodium hydroxide solution and ethanol as needed. The reaction mixture was kept at room temperature until all of the keto-acid was consumed (it may be necessary to add a further portion of the more volatile alkoxyamines). The progress of the reaction was followed by acidification of an aliquot, extraction with ethyl acetate and thin layer chromatography of the extract on silica plates (developed with a mixture of chloroform: methanol: acetic acid; 18:2:1). The alkoxyiminoacetic acids were less polar than the starting keto-acids. The reaction times were 2 hours to 2 days. When reaction was complete the pH of the mixture was adjusted to between 7 and 8 and the ethanol (if any) was removed by evaporation. The aqueous mixture was extracted with ether, the extract discarded and the aqueous phase acidified to pH <2 with dilute hydrochloric acid. The mixture was extracted with ethyl acetate or ether, the extract dried and evaporated to give the crude product which was purified by one of the following methods:

a. Crystallisation and recrystallisation (if needed) from a suitable solvent.

b. The crude product dissolved in ether was treated with a small excess of a solution of diazomethane in ether. The excess reagent was destroyed with acetic acid and the solution washed with sodium bicarbonate solution and evaporated to give the crude methyl esters. The esters were separated by preparative thick layer chromatography or column chromatography on silica, and then hydrolysed conventionally with alkali to give the syn acids, which were purified by crystallisation from a suitable solvent.

These methods were employed to prepare the intermediates listed in Table 3 (syn-isomers).

TABLE 3

| Preparation No. | R | R" | Purification (solvent) | Mp ° | $\tau$ values (DMSO-d$_6$) R | R" | $\lambda$max. nm (EtOH) | $\epsilon$ |
|---|---|---|---|---|---|---|---|---|
| 44 |  |  | (b) (cyclohexane) | 71.2 | 2.30, 2.7–3.0 | 5.25, 7.9–8.6 | 291.5 | 10,900 |
| 45 |  | —C(CH$_3$)$_3$ | (a) (cyclohexane) | 124.5–125.5 | 2.1–2.45, 2.45–2.85, 2.78 | 8.66 | 232.5, 296, 307.5 | 6,700; 25,400; 23,500 |
| 46 |  | —CH$_3$ | (a) (benzene) | 114–115 | 3.03, 3.77, 3.92, 6.16 | 6.24 | 286 | 16,200 |

TABLE 3-continued

| Preparation No. | R | R" | Purification (solvent) | Mp ° | τ values (DMSO-$d_6$) R | τ values (DMSO-$d_6$) R" | λmax. nm (EtOH) | ε |
|---|---|---|---|---|---|---|---|---|
| 47 | (pyrrole-N-CH₃) | —C(CH₃)₃ | (a) | 146–147 (benzene) | 3.00, 147 | 8.66 3.75, 3.90, 6.16 | 284 | 16,000 |

PREPARATION 48

2-(Thien-2-ylmethoxyimino)-(1-methylpyrrol-2-yl)acetic acid (syn-isomer)

A solution of 1-methylpyrrol-2-ylglyoxylic acid (4.6 g) and thien-2-ylmethoxamine hydrochloride (5.46 g) in aqueous ethanol (100 ml, 1:1) was adjusted to pH 4.8 with 10N-sodium hydroxide solution and stirred at pH 4.8 for 24 hours at room temperature. A further portion of thein-2-ylmethoxamine (0.5 g) was added and the solution was maintained at pH 4.8 and room temperature for a further 2 days. The pH was then adjusted to 8 with sodium bicarbonate solution and the ethanol was removed by evaporation. The aqueous residue was washed with ether and the aqueous phase was acidified to pH 1.5 under ether with 2N-hydrochloric acid. The ether extracts were combined and washed with water, dried and evaporated to give an orange oil (8.8 g). The crude mixture of syn and anti-isomer was esterified with a slight excess of diazomethane in ether.

To a solution of the mixed methyl esters (7.7 g) in methanol (100 ml) was added N-sodium hydroxide (28 ml). The mixture was kept at room temperature for 3 hours when thin-layer chromatography of an aliquot showed only traces of remaining anti-ester. After a further 30 minutes 2N-hydrochloric acid (14 ml) was added and the methanol was removed by evaporation. The residue was partitioned between ether and excess sodium bicarbonate in water. The ether layer was separated, washed with water, dried and evaporated to a pale orange oil (5.9 g).

This oil in methanol (100 ml) was treated with 10N-sodium hydroxide solution (4.5 ml) and kept at room temperature for 16 hours. A further portion of 10N-sodium hydroxide solution (4.5 ml) was added and after 24 hours at room temperature the mixture was warmed to 60° for 30 minutes. The methanol was removed by evaporation and the residue divided between ether and sodium bicarbonate solution. The aqueous phase was acidified under ether with 2N-hydrochloric acid. The combined ether extracts were washed with water and dried. Evaporation of the ether gave a pale orange oil (4.8 g) which was crystallised from carbon tetrachloride to give the title compound as pale brown crystals (1.9 g); m.p. 70°–71; λ$_{max.}$ (EtOH) 235, 287.5 nm (ε 11,600 and 17,100); τ (DMSO-$d_6$) values include 4.70 (S, CH$_2$) and 6.18 (S, Ch$_3$).

General Method for Converting a 2-Substituted-oxyimino-2-arylacetic Acid into its Acid Chloride without Isomerisation A solution of the pure syn-2-substituted-osyimino-2-arylacetic acid (1 equiv.) in methanol (ca. 2–4 ml/mmole) was treated with sodium methoxide (1 equiv.) in methanol at 0°–25 ° and the mixture evaporated to give the sodium salt which may be dried by azeotroping with several portions of benzene and/or drying in vacuo over phosphorus pentoxide.

The anhydrous sodium salt (1 equiv.) was suspended in dry benzene (ca. 5 ml/mmole) containing a few drops of dry dimethylformamide and treated with freshly distilled oxalyl chloride (1–2.5 equiv.). The mixture was stirred at room temperature for 0.5–1 hour and then evaporated to remove benzene. The resulting acid chlorides were not characterised but were dissolved in acetone and used immediately to acylate the appropriate penicillin nucleus.

The acids described in Preparations 40–48 were converted into their acid chlorides in this way.

PREPARATION 49

Cyclopentyloxamine hydrochloride

A mixture of bromocyclopentane (14.9 g), N-hydroxyphthalimide (16.3 g), triethylamine (15 ml), and dimethylformamide (30 ml) was stirred for 16 hours, then poured into water (500 ml). The oily mixture was extracted with ethyl acetate, and the combined extracts, after washing (water), drying, and removal of solvent gave a white solid. This solid was recrystallised from ethanol to give N-cyclopentyloxyphthalimide (11.37 g, 49%); m.p. 81.2°–82.5°; ν$_{max.}$ (CHBr$_3$) include 1780, 1720 cm$^{-1}$ (CO-N-CO), 970 cm$^{-1}$ 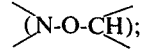 ;

τ values (DMSO-d6) 2.08 (4 Ar-H), 5.12 (cyclopentyl 1-H), 8.18 (4-CH$_2$).

A mixture of N-cyclopentyloxyphthalimide (11 g), 100% hydrazine hydrate (2.6 g), and ethanol (30 ml) was heated under reflux for 5 minutes. Concentrated hydrochloric acid (6 ml) was added to the mixture, which was heated under reflux for a further 5 minutes. Water (20 ml) was added to the mixture, which was cooled to room temperature, and filtered. The filtrate was evaporated to dryness, ethanol (50 ml) was added to the residue, and a small amount of insoluble material was filtered off. The filtrate was evaporated to dryness, and the residue was recrystallised from ethanol/ether to give cyclopentyloxamine hydrochloride (6.28 g, 96%), m.p. 156.9°.

PREPARATION 50 syn-Isopropoxyiminophenylacetic acid

A mixture of phenylglyoxylic acid (3.0 g.), isopropoxyamine hydrochloride (2.5 g.), ethanol (100 ml) and water (50 ml) was stirred and adjusted to pH 4.5 to 5 with sodium hydroxide solution (2N). The solution was stirred for 5 hr. maintaining the pH at 4.5–5 with further additions of sodium hydroxide solution. The ethanol was removed by evaporation, the aqueous residue acidified and the product collected by extraction with ethyl acetate. Evaporation of the ethyl acetate gave a brown oil (4.2 g.). that was esterified conventionally with diazomethane to give a mixture of the syn and anti methyl esters of the title compound as an oil (4.04 g.).

The mixture of ester (4.0 g) in methanol (60 ml) was treated with sodium hydroxide solution (2N:19.0 ml) and kept for 2 hr. at room temperature. The methanol was evaporated and the residue, diluted with water, extracted with ethyl acetate. Evaporation of the dried ($MgSO_4$) ethyl acetate solution gave the crude syn methyl ester (0.82 g.). The ester (0.82 g) in methanol (20 ml) was treated with sodium hydroxide solution (2N:3.6 ml) and kept at room temperature for 31 hr. Conventional isolation of acidic material gave the crude syn isomer (0.706 g) which was recrystallised from cyclohexane to give the title compound (0.358 g.) m.p. 59.5° $\lambda_{max}$. (EtOH) 258 nm ($\epsilon$ 12,700), $\tau$ (DMSO-$d_6$) values include 2.47 (phenyl), 5.53 (O—CH<), 8.71 ($CH_3$).

EXAMPLE 1

6$\beta$-(2-Methoxyimino-2-phenylacetamido)-2,2-dimethylpenam-3$\Delta$-carboxylic acid (syn-isomer)

To a cold (0°–5°) solution of 6$\beta$-aminopenicillanic acid (0.91 g.) in acetone (10 ml) and water (10 ml) containing sodium bicarbonate (0.735 g.) was added a solution of syn 2-methoxyiminophenylacetyl chloride (0.91g.) in acetone (10 ml) over a period of 10 minutes. The mixture was stirred at 0°–5° for 30 minutes, evaporated to remove acetone, and the solution washed with cold ethyl acetate and then poured into a cold stirred mixture of 2N-hydrochloric acid and ethyl acetate. The layers were separated, and the aqueous phase was washed with ethyl acetate. The organic extracts were combined, dried, and evaporated to a froth (1.63 g.) which was triturated with petroleum (b.p. 60°–80°) producing a pale yellow solid (1.52 g.). This was purified by preparative plate chromatography using chloroform: methanol (4:1) as developing solvent, producing a solid (0.77 g.). This was triturated with ether to remove some insoluble material, and then crystallised by the addition of petroleum spirit (b.p. 60°–80°) producing the title compound (0.49 g., 32%), $[\alpha]_D^{26} + 195°$ (c, 0.72 dioxan), $\lambda_{max}$. (pH 6.0 phosphate buffer), 259 nm ($\epsilon$ 9,400), $\nu_{max}$. (Nujol), 1765 ($\beta$-lactam), 1730 ($CO_2H$), 1640, 1528 cm.$^{-1}$ (CONH); $\tau$ (DMSO-$d_6$) 0.27 (doublet J 7.0 Hz; NH), 2.3–2.6 (multiplet, Ph), 6.06 (singlet $OCH_3$), 8.38 and 8.47 (singlets, $CH_3$ groups).

EXAMPLE 2

6$\beta$-(2-t-Butoxyimino fur-2'-ylacetamido)-2,2-dimethylpenam-3$\alpha$-carboxylic acid (syn-isomer)

syn-t-Butoxyimino fur-2-ylacetic acid (2.11 g) was treated with sodium methoxide solution (0.525 M : 19.1 ml.) at room temperature. Evaporation of the methanol gave a buff sodium salt that was dried over phosphorus pentoxide overnight. The sodium salt (933 mg.) in dry benzene (10 ml.) containing dimethylformamide (1 drop) was treated with oxalyl chloride (0.8 ml.) at room temperature for 1 hr. The solvent was removed by evaporation and the residue in acetone (20 ml) was added dropwise to a solution of 6$\beta$-aminopenicillanic acid (864 mg.) and sodium bicarbonate (672 mg.) in water (50 ml) at 0°–5°C. The resulting solution was stirred at room temperature for 1½ hr. The acetone was removed by evaporation and the aqueous phase adjusted to pH 8.5 and washed with ether. The aqueous layer was then acidified to pH 2 under ether and the ether layer was washed with water, dried and evaporated to give a pale yellow foam. This was dried to give the title compound (1.42 g., 87%), $[\alpha]_D + 188°$ (c 1, dioxan), $\lambda_{max}$. (pH 6 phosphate buffer) 287.5 nm ($\epsilon$ 14,400), $\nu_{max}$. (CHBr$_3$) 1774 ($\beta$-lactam), 1670 and 1510 cm.$^{-1}$ (CONH), $\tau$ (DMSO-$d_6$) values include 0.48 (d, J 8 Hz, NH), 2.16 and 3.32 (fur-2-yl protons), 8.70 (C($CH_3$)$_3$).

EXAMPLE 3

6$\beta$-(2-t-Butoxyiminobenzo[b]thien-3'-ylacetamido)-2,2-dimethylpenam-3$\alpha$-carboxylic acid (syn-isomer)

syn-t-Butoxyiminobenzo[b] thien-3-ylacetic acid (525 mg.) was treated with sodium methoxide solution (0.445 M: 4.5 ml.) at room temperature. The solvent was removed by evaporation and the resulting solid was dried over phosphorus pentoxide. The sodium salt in dry benzene 910 ml.) containing dimethylformamide (1 drop) was treated with oxalyl chloride (0.4 ml.) at room temperature for 1 hr. The solvent was removed by evaporation and the residue in acetone (25 ml) was added dropwise to a solution of 6$\beta$-aminopenicillanic acid (432 mg.) and sodium bicarbonate (420 mg.) in water (25 ml.) at room temperature. The resulting pale yellow suspension was stirred at room temperature for 3 hr. The mixture was diluted with water and washed with ether. The aqueous phase was acidified to pH 2 under ether. The ether layer was washed with water and dried. Evaporation gave the title compound as a pale yellow foam (280 mg., 30%), $[\alpha]_D + 209°$ (c 1, dioxan), $\lambda_{max}$. (pH 6 phosphate buffer) 226, 297 nm ($\epsilon$ 22,400; 10,900), $\nu_{max}$. (CHBr$_3$) 1786 ($\beta$-lactam), 1680 and 1516 cm.$^{-1}$ (CONH), $\tau$ (DMSO-$d_6$) values include 0.41 (d, J 8 Hz, NH), 4.21 (q, 7-proton), 8.56 (C($CH_3$)$_3$).

EXAMPLES 4–26 and 36–56

General Procedures for the Preparation of 6$\beta$-(2-Substituted oxyimino-2-arylacetamido)-2,2-dimethylpenam-3$\alpha$-carboxylic Acids.

Method A

A solution of the appropriate 2-substituted-oxyimino-2-arylacetyl chloride (prepared from 1 equiv.

of the corresponding sodium salt with oxalyl chloride) was dissolved in acetone and the solution was added dropwise to a stirred, ice-cold (0°–5°) solution of 6β-aminopenicillanic acid (1 equiv.) in water containing sodium bicarbonate (2–2.5 equiv.). The mixture was stirred for 30 min.–3hr. allowing the temperature to rise to room temperature. Acetone was removed by evaporation under reduced pressure, the pH was adjusted to ca. 1.5–2.0 and the product was extracted into ether. The extracts were washed with water and saturated brine, dried and evaporated to a foam at low temperature.

Method B

As above but the product was isolated by extraction with ethyl acetate in place of ether.

Method C

As in Method A but the sodium salt was extracted into ethyl acetate and the extract washed successively with 2N-hydrochloric acid, and water, dried and evaporated to a foam.

Method D

A solution of the appropriate acid chloride (from 1 equiv. of the sodium salt) was dissolved in dry methylene chloride (ca. 5 ml/mmole) and the solution was added to a suspension of 6β-aminopenicillanic acid (1 equiv.) and triethylamine (3 equivs.) in methylene chloride at 0°–5° with stirring. After stirring at room temperature for ca. 1.5 hr. the solution was evaporated to dryness, dissolved in water, washed with ethyl acetate and the aqueous layer acidified to pH 1.5 under ethyl acetate. The extracts were washed with water and brine and evaporated to a foam.

TABLE 4

| Ex. No. | R | R" | Method | $[\alpha]_D$ (dioxan) | pH 6 $\lambda_{max}$ nm (solvent) | $\epsilon$ | β-lactam $\nu_{max}$ cm.$^{-1}$ x | τ values for DMSO-$d_6$ at 100 MHz R" | | y | Yield % |
|---|---|---|---|---|---|---|---|---|---|---|---|
| 4 | Ph | $C_2H_5$ | B | +168° | 257.5 | 9,900 | 1770 (Nujol) | 0.32 | 5.78 ($CH_2$) 8.70 ($CH_3$) | 4.26 | 90 |
| 5 | Ph | $C(CH_3)_3$ | D | +117° | 257.5 | 10,200 | 1780 ($CHBr_3$) | 0.59 | 8.66 | 4.25 | 84 |
| 6 | Ph | $CH_2Ph$ | D | +120° | 245 | 11,100 | 1780 ($CHBr_3$) | 0.23 | 4.77 ($CH_2$) | 4.27 | 88 |
| 7 | Ph | $CH_2$–(thien-2-yl) | B | +108° | 236.5 | 15,000 | 1770 (Nujol) | 0.25 | 4.63 ($CH_2$) 2.5, 2.76 and 2.97 (thien-2-yl) | 4.30 | 77 |
| 8 | (thien-2-yl) | $CH_3$ | A | +140° | 294 | 13,600 | 1778 ($CHBr_3$) | 0.22 | 6.09 | 4.32 | 88 |
| 9 | (thien-2-yl) | $C_2H_5$ | B | +170° | 294 | 9,800 | 1772 (Nujol) | 0.20 | 5.86 ($CH_2$) 8.75 ($CH_3$) | 4.33 | 62 |
| 10 | (thien-2-yl) | $C(CH_3)_3$ | B | +182° | 265 294 | 11,300 12,500 | 1780 (Nujol) | 0.47 | 8.71 | 4.31 | 68 |
| 11 | (thien-2-yl) | $CH_2Ph$ | B | +179° | 264 272 295 | 5,500 8,800 11,500 | 1786 (Nujol) | 0.17 | 4.84 ($CH_2$) 2.61 (Ph) | 4.33 | 44 |
| 12 | (thien-2-yl) | $CH_2$–(thien-2-yl) | B | +195° | 231 295.5 | 11,900 11,500 | 1776 (Nujol) | 0.20 | 4.67 ($CH_2$) | 4.35 | 96 |
| 13 | (thien-2-yl) | $CHOCH_2CH_3$ $CH_3$ | B | +181° | 292 | 10,350 | 1772 (Nujol) | 0.29 | 6.30 ($CH_2$) 8.88 ($CH_2CH_3$) 8.66 ($CH_3$) | 4.30 | 75 |
| 14 | (2-Cl-phenyl) | $CH_3$ | A | +120° | 240 (inf.) | 8,000 | 1784 ($CHBr_3$) | 0.60 | 6.01 | 4.29 | 90 |
| 15 | (naphthyl) | $CH_3$ | B | +189° | 291 | 6,300 | 1780 (Nujol) | 0.22 | 6.00 | 4.32 | 65 |
| 16 | (naphthyl) | $C(CH_3)_3$ | C | +197° | 297 | 8,000 | 1788 (Nujol) | 0.42 | 8.59 | 4.24 | 89 |
| 17 | (naphthyl) | $CH_2Ph$ | C | +141° | 292.5 | 7,300 | 1776 (Nujol) | 0.12 | 4.67 ($CH_2$) | 4.27 | 98 |

TABLE 4-continued

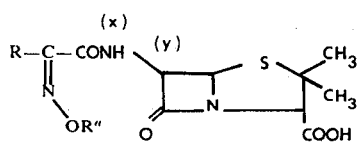

| Ex. No. | R | R" | Method | $[\alpha]_D$ (dioxan) | pH 6 $\lambda_{max.}$ nm (solvent) | ε | β-lactam $\nu_{max}$ cm.$^{-1}$ | τ values for DMSO-d$_{65\,6}$ at 100 MHz | | Yield % |
|---|---|---|---|---|---|---|---|---|---|---|
| | | | | | | | x | R" | y | |
| 18 | (thienyl) | CH$_3$ | B | +151° | 223.5 298 | 22,500 9,400 | 1770 (CHBr$_3$) | 0.24 | 5.99 | 4.28 | 74 |
| 19 | (furyl) | CH$_3$ | A | +211° | 284.5 | 13,600 | 1772 (CHBr$_3$) | 0.25 | 6.09 | 4.34 | 78 |
| 20 | (furyl) | CH$_2$Ph | A | +171° | 286.5 | 16,000 | 1782 (CHBr$_3$) | 0.20 | 4.79 (CH$_2$) 2.59 | 4.32 (Ph) | 92 |
| 21 | (benzothienyl) | CH$_2$Ph | A | +195° | 306 | 22,600 | 1780 (CHBr$_3$) | 0.06 | 4.73 (CH$_2$) 2.56 (Ph) | 4.26 | 79 |
| 22 | (benzothienyl) | CH$_3$ | A | +201° | 229 305 | 15,700 21,200 | 1780 (CHBr$_3$) | 0.13 | 6.05 | 4.26 | 90 |
| 23 | (thienyl) | CH$_2$CH$_2$Br | B | +189.5 | 294.5 | 10,800 | 1780 (Nujol) | 0.27 | 5.60;6.32 | 4.30 | 88 |
| 24 | (furyl) | CH$_2$(furyl) | B | +108° | 285 | 14,700 | 1780 (Nujol) | 0.26 | 4.90;2.3; 3.4–3.6 (furyl protons) | 4.38 | 92 |
| 25 | (furyl) | CH$_2$(thienyl) | A | +198 | 277.5 285.5 | 12,700 16,100 | 1788 (CHBr$_3$) | 0.28 | 4.68;2.14; 3.25;3.36 (thienyl protons) | 4.38 | 80 |
| 26 | (furyl) | C$_2$H$_5$ | A | +252 | 284 | 15,200 | 1788 (CHBr$_3$) | 0.28 | 5.77;8.71 | 4.30 | 68 |
| 36 | Ph | n-C$_4$H$_9$ | B | +194 | 259 | 10,200 | 1770 (Nujol) | 0.37 | 5.83,8.2–8.9,9.01 | 4.26 | 83 |
| 37 | Ph | CH(CH$_3$)$_2$ | B | +202 | 259 | 10,200 | 1780 (Nujol) | 0.41 | 5.57,8.20 | 4.26 | 51 |
| 38 | (thienyl) | C$_2$H$_5$ | B | +160° | 253 264.5 | 2,000 11,750 | 1780 (Nujol) | 0.40 | 5.82,8.73 | 4.36 | 95 |
| 39 | (benzofuryl) | C$_2$H$_5$ | B | +200° | 232.5 inf. 303 | 7,950 23,600 | 1775 (CHBr$_3$) | 0.28 | 5.73,8.71 | 4.15 | 77 |
| 40 | (furyl) | Ph | B | +198° | 275 296.5 | 10,200 13,500 | 1782 (Nujol) | −0.01 | 2.5–2.9 | 4.28 | 87 |
| 41 | (thienyl) | Ph | B | +196° | 267 305 | 9,400 10,850 | 1774 (Nujol) | −0.08 | 2.4–2.8 | 4.23 | 97 |
| 42 | (furyl) | (cyclobutyl) | B | +190° | 285 | 14,500 | 1782 (Nujol) | 0.48 | 5.29 and 7.9–8.6 | 4.36 | 96 |
| 43 | (thienyl) | (cyclobutyl) | B | +195° | 296 | 11,000 | 1788 (Nujol) | 0.39 | 5.29 and 8.0–8.7 | 4.35 | 95 |
| 44 | (benzofuryl) | Bu$^t$ | A | +195° | 302 | 24,100 | 1776 | 0.32 | 8.61 | 4.22 | 93 |

TABLE 4-continued

| Ex. No. | R | R" | Method | $[\alpha]_D$ (dioxan) | pH 6 $\lambda_{max.}$ nm (solvent) | $\epsilon$ | β-lactam $\nu_{max}$ cm.$^{-1}$ x (CHBr$_3$) | τ values for DMSO-d$_{6}$ at 100 MHz R" y | | Yield % |
|---|---|---|---|---|---|---|---|---|---|---|
| 45 |  | CH$_3$ | A | +223° | 296 | 11,200 | 1780 (CHBr3) | 0.54 | 6.23 | 4.39 | 83 |
| 46 |  | C(CH$_3$)$_3$ | A | +214° | 292 | 13,500 | 1784 (CHBr$_3$) | 0.72 | 8.68 | 4.32 | 89 |
| 47 | 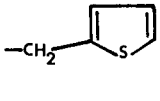 | —CH$_2$ | A | +175° | 232 297.5 | 13,100 12,600 | 1786 (CHBr$_3$) | 0.47 | 4.72 (CH$_2$) | 4.38 | 51 |

TABLE 5

| Ex. No. | R | R" | Method | $[\alpha]_D$ (dioxan) | pH 6 $\lambda_{max.}$ nm | $\epsilon$ | β-lactam $\nu_{max}$ cm.$^{-1}$ (solvent) | τ values for DMSO-d$_6$ at 100 MHz x R" y | | | Yield % |
|---|---|---|---|---|---|---|---|---|---|---|---|
| 48 | Ph | CH$_3$ | B | +140° | 240 (inf.) | 8,700 | 1780 (CHBr$_3$) | 1.32 | 6.01 | 4.2–4.5 | |
| 49 | Ph | C$_2$H$_5$ | B | +148° | 245 (inf.) | 8,800 | 1778 (Nujol) | 1.38 | 5.75 (CH$_2$) 8.73 (CH$_3$) | 4.33 | 80 |
| 50 | Ph | CH$_2$Ph | A | +115° | 240 (inf.) | 10,200 | 1778 (CHBr$_3$) | 1.44 | 4.72 (CH$_2$) | 4.32 | 88 |
| 51 |  | CH$_3$ | A | +156° | 235 (inf.) | 9,100 | 1780 (CHBr$_3$) | 1.68 | 6.01 | 4.34 | 96 |
| 52 |  | C(CH$_3$)$_3$ | D | +121° | 250 (inf.) | 8,880 | 1780 (CHBr$_3$) | 1.95 | 8.72 | 4.3 | 90 |
| 53 |  | CH$_2$Ph | D | +111° | 240 (inf.) | 9,600 | 1778 (CHBr$_3$) | 1.80 | 4.7 (CH$_2$) 2.6 (Ph) | 4.3 | 68 |
| 54 |  | CH$_3$ | B | +149° | 268.5 277.5 290 | 27,600 25,400 18,800 | 1780 (Nujol) | 1.29 | 6.05 | 4.32 | 83 |

TABLE 5-continued

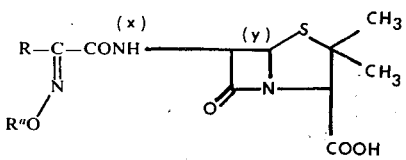

| Ex. No. | R | R" | Method | $[\alpha]_D$ (dioxan) | pH 6 $\lambda_{max}$ nm | $\epsilon$ | $\beta$-lactam $\nu_{max}$ cm.$^{-1}$ (solvent) | \multicolumn{3}{c}{$\tau$ values for DMSO-d$_6$ at 100 MHz} | Yield % |
| --- | --- | --- | --- | --- | --- | --- | --- | --- | --- | --- | --- |
| | | | | | | | | x | R" | y | |
| 55 | (naphthyl) | CH$_2$Ph | B | +120° | 268 278.5 | 7,300 14,000 | 1782 (Nujol) | 1.46 | 4.79 (CH$_2$) 2.66 (Ph) | 4.34 | 57 |
| 56 | (thienyl) | Ph | B | +149° | 300 | 11,700 | 1770 (Nujol) | 0.28 | 2.6 | 4.2–4.4 | 96 |

EXAMPLE 57

6$\beta$-(2-Methoxyimino-2-phenylacetamido)-2,2-dimethylpenam-3$\alpha$-carboxylic Acid (syn-isomer)

A solution of syn-2-mthoxyimino-2-phenylacetic acid (1 g.) in dry methylene chloride (10 ml.) containing triethylamine (0.775 ml.) was stirred and cooled to 0°. To this solution was added a solution of pivaloyl chloride (0.686 ml.) in dry methylene chloride (10 ml.) over 10 minutes. The solution was stirred at 0° for 1 hour, and at room temperature for 1 hour, and cooled to 0° and treated with a cooled suspension of 6$\beta$-aminopenicillanic acid (1.81 g.) in dry methylene chloride (10 ml.) containing triethylamine (1.68 g.). The mixture was stirred at 0° for 1½ hours, and at room temperature for 2 hours. The solution was evaporated to dryness, and the oil dissolved in saturated sodium bicarbonate solution (50 ml.). The solution was washed with ethyl acetate. The aqueous solution under ethyl acetate (30 ml.) was acidified to pH 3 with 2N-hydrochloric acid. The layers were separated, and the aqueous phase washed with ethyl acetate. The organic extracts were combined, dried, and evaporated to a yellow oil (3.1 g.). This was purified by preparative plate chromatography (silica) using chloroform-methanol (4:1) as developing solvent. Elution of the main band and evaporation gave a foam which was dissolved in ether, filtered and the filtrate diluted with petroleum spirit (bp. 60°–80°) to precipitate a solvated sample of the title compound (0.48 g., 24%), $[\alpha]_D$ + 170° (c 0.86 dioxan), $\lambda_{max}$ (pH 6 phosphate buffer) 257 nm ($\epsilon$ 9,450), $\nu_{max}$ (Nujol) 1765 ($\beta$-lactam), $\tau$ (DMSO-d$_6$) 0.32 (doublet, NH), 6.1 OCH$_3$).

EXAMPLE 58

6$\beta$-(2-Phenoxyimino-2-phenylacetamido)-2,2-dimethylpenam-3$\alpha$-carboxylic acid (syn-isomer)

A solution of syn-2-phenoxyiminophenylacetic acid (362 mg) in methanol (2.5 ml) was neutralised with 0.575 N sodium methoxide solution (2.61 ml). Removal of the solvent gave the sodium salt, which, after drying in vacuo over phosphorus pentoxide, was suspended in benzene (10 ml) containing N,N-dimethylformamide (one drop), and stirred with oxalyl chloride (0.26 ml) for 0.5 hours. The mixture was evaporated to dryness and the residue, dissolved in acetone (15 ml), was added dropwise to a stirred, ice-cooled solution of 6$\beta$-aminopenicillanic acid (324 mg) in water (25 ml) and acetone (10 ml), containing sodium bicarbonate (252 mg). The resulting solution was stirred for 1.25 hours, the acetone was evaporated, and the aqueous residue was acidified to pH 2.0 under ethyl acetate. The acidic mixture was extracted with ethyl acetate. The combined extracts were washed (water, saturated brine), dried, and evaporated to give the ethylacetate solvated title compound (674 mg, 90%); $[\alpha]_D^{22}$ + 200° (c 0.98, dioxan); $\lambda_{max}$ (pH6 buffer) 260, 285.5 nm ($\epsilon$9,700; 8,750); $\nu_{max}$ (Nujol) 3270 (NH), 1780 cm$^{-1}$ ($\beta$ lactam); $\tau$ values (DMSO-d6) include 0.02 (NH), 4.21 (6-H), 4.33 (5-H).

The following Examples serve to illustrate the formulation of pharmaceutical preparations.

EXAMPLE A

Dry Powder for Injection

Sterile sodium 6$\beta$-(2-methoxyimino-2-phenylacetamido)-2,2-dimethylpenam-3$\alpha$-carboxylate (synisomer) powder was filled into glass vials, the claimed fill weights being 500 mg. and 1.0 g antibiotic. Filling was carried out aseptically under a blanket of nitrogen. The vials were closed using rubber discs held in position by aluminium sealing rings, thereby preventing gaseous exchange or ingress of micro-organisms. The product was intended for reconstitution with Water for Injections or other suitable sterile vehicle shortly before administration.

EXAMPLE B

Intramammary Infusion for Cattle

Percentage composition (w/w):

| | | |
| --- | --- | --- |
| 6$\beta$-(2-t-Butoxyimino-2-phenylacetamido)-2,2-dimethylpeham-3$\alpha$-carboxyic acid (syn-isomer) | 10.00 | as sodium salt |
| Vehicle to: | 100.00 | |
| Vehicle: Tween 60 | 3.00 | |
| White Beeswax | 6.00 | |
| Arachis Oil | 91.00 | |

The three ingredients of the vehicle were heated together at 150°C for 1 hour and then cooled to room temperature with stirring. The sterile antibiotic powder was added aseptically to this vehicle and the product refined with a high speed stirrer. The preparation was filled aseptically into sterile collapsible aluminium tubes with a fill weight of 3.0 g., each tube containing 300 mg. penicillin derivative.

EXAMPLE C

Dry Blend for an Oral Syrup

| | | |
|---|---|---|
| 6β-(2-Methoxyimino-2-phenylacetamido)-2,2-dimethylpenam-3α-carboxylic Acid (syn-isomer) | 5.00 g. | as sodium salt |
| Sodium Saccharin | 0.10 g. | |
| Sodium Citrate (anhydrous) | 1.00 g. | |
| Citric Acid (anhydrous) | 0.10 g. | |
| Amaranth | 0.01 g. | |
| Spray-dried Raspberry Flavour | 1.00 g. | |
| Sucrose | to 75.00 g. | |

The product was intended for reconstitution with sufficient Purified Water to give a final volume of 100 ml, which would all be administered within a few days, each 5 ml. dose of syrup containing 250 mg. Penicillin derivative.

In order to prepare the blend, the Amaranth was intimately mixed with some of the Sodium Citrate and milled. The sodium saccharin and citric acid were bended together. They were mixed thoroughly with the colour triturate, then with the remainder of the sodium citrate, flavour and antibiotic powder in that order. This blend was milled, mixed with sucrose and then 75 g. filled into each of a number of 150 ml. capacity bottles, which were closed with moisture-proof screw caps.

EXAMPLE D

Oral Capsules

The antibiotic was blended with one percent magnesium stearate and filled into size 0 hard gelatin capsules, each capsule containing a claimed dose of 250 mg. Sodium 6β-(2-methoxyimino-2-phenylacetamido)-2,2-dimethylpenam-3α-carboxylate (syn-isomer). The capsules were packed in glass vials with plastic caps giving a moisture-proof seal.

We claim:
1. A penicillin antibiotic of the formula

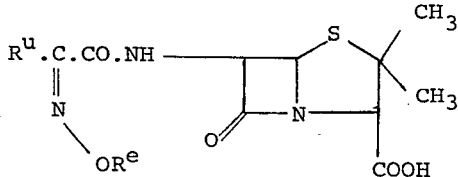

wherein $R^u$ is furyl; benzofuryl or either of these groups substituted by chlorine, bromine, iodine, fluorine, hydroxy, lower alkyl, nitro, amino, lower alkylamino, diloweralkylamino, lower alkanoyl, lower alkanoylamino, lower alkoxy, lower alkylthio or carbamoyl and $R^e$ is alkyl of 1–16 carbon atoms; alkenyl of 2–16 carbon atoms; alkynyl of 2–16 carbon atoms; cycloalkyl of 3–7 carbon atoms; cycloalkenyl of 4–7 carbon atoms; phenyl; naphthyl; a heterocyclic radical selected from the group consisting of thienyl; furyl; pyridyl; pyrimidyl; pyrrolyl; N-methylpyrrolyl; N-benzyloxymethylpyrrolyl; thiazolyl; isothiazolyl; diazolyl; triazolyl; tetrazolyl; thiadiazolyl; thiatriazolyl; oxazolyl; oxadiazolyl; 3- or 4-isoxazolyl; sydnone; benzothienyl; benzofuryl; indolyl; benzimidazolyl; benzoxazolyl and purinyl; phenyl lower alkyl; diphenylmethyl; triphenylmethyl; naphthyl lower alkyl; heterocyclic lower alkyl in which the heterocyclic moiety is derived from said heterocyclic radical, or any of these groups substituted by hydroxy, lower alkoxy, phenoxy, benzyloxy, mercapto, lower alkylthio, phenylthio, benzylthio, amino, chlorine, bromine, iodine, fluorine, nitro, azido, carboxy, lower carbalkoxy, formyl, acetyl, propionyl, benzoyl, acetoxy, propionyloxy, pivaloyloxy, cyano, phthalimido, acetamdio, benzamido, lower alkoxycarbonylamino or benzyloxycarbonylamino; or a physiologically acceptable salt thereof.

2. A penicillin antibiotic of the formula

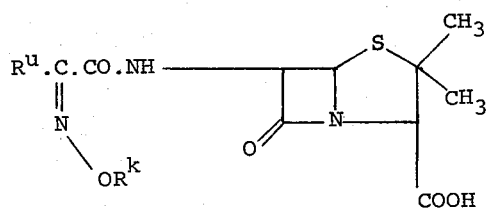

wherein $R^u$ is furyl; benzofuryl or either of these groups substituted by clorine, bromine, iodine, fluorine, hydroxy, lower alkyl, nitro, amino, lower alkylamino, diloweralkylamino, lower alkanoyl, lower alkanoylamino, lower alkoxy, lower alkylthio or carbamoyl and $R^k$ is methyl or ethyl or a physiologically acceptable salt thereof.

3. A penicillin antibiotic of the formula

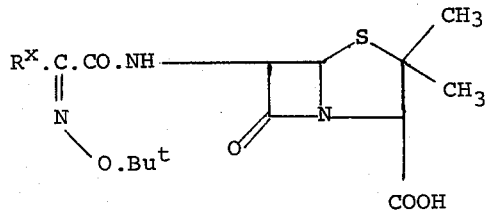

wherein $R^x$ is furyl or benzofuryl and $Bu^t$ is tert-butyl or a physiologically acceptable salt thereof.

4. The compound of claim 1 which is 6β-[2-t-butoxyimino-2-(benzo-[b]-fur-2-yl)-acetamido]-2,2-dimethylpenam-3α-carboxylic acid (syn-isomer).

5. The compound of claim 1 which is 6β-[2-methoxyimino-2-(fur-2-yl)acetamido]-2,2-dimethylpenam-3α-carboxylic acid (syn-isomer).

6. The compound of claim 1 which is 6β-[2-t-butoxyimino-2-(fur-2-yl)acetamido]-2,2-dimethylpenam-3α-carboxylic acid (syn-isomer).

7. The compound of claim 1 which is 6β-[2-benzyloxyimino-2-(fur-2-yl)acetamido]-2,2-dimethylpenam-3α-carboxylic acid (syn-isomer).

8. The compound of claim 1 which is 6β-[2-furfuryloxyimino)-2-(fur-2-yl)acetamido]-2,2-dimethylpenam-3α-carboxylic acid (syn-isomer).

9. The compound of claim 1 which is 6β-[2-(thien-2-yl)methoxyimino)-2-(fur-2-yl)acetamido]-2,2-dimethylpenam-3α-carboxylic acid (syn-isomer).

10. The compound of claim 1 which is 6β-[2-ethoxyimino-2-(fur-2-yl)acetamido]-2,2-dimethylpenam-3α-carboxylic acid (syn-isomer).

11. The compound of claim 1 which is 6β-[2-ethoxyimino-2-(benzo-[b]-fur-2-yl)-acetamido]-2,2-dimethylpenam-3α-carboxylic acid (syn-isomer).

\* \* \* \* \*